US008735061B2

(12) United States Patent
Lou et al.

(10) Patent No.: US 8,735,061 B2
(45) Date of Patent: May 27, 2014

(54) BIOMARKERS OF CANCER METASTASIS

(75) Inventors: Yuanmei Lou, Vancouver (CA); Paul Christopher McDonald, Coquitlam (CA); Arusha Oloumi, West Vancouver (CA); Shoukat Dedhar, Richmond (CA)

(73) Assignee: British Columbia Cancer Agency Branch, Vancouver (CA)

( * ) Notice: Subject to any disclaimer, the term of this patent is extended or adjusted under 35 U.S.C. 154(b) by 0 days.

(21) Appl. No.: 13/572,067

(22) Filed: Aug. 10, 2012

(65) Prior Publication Data
US 2012/0301891 A1 Nov. 29, 2012

Related U.S. Application Data

(62) Division of application No. 12/795,269, filed on Jun. 7, 2010, now abandoned.

(60) Provisional application No. 61/184,380, filed on Jun. 5, 2009.

(51) Int. Cl.
*C12Q 1/68* (2006.01)
*G01N 33/53* (2006.01)

(52) U.S. Cl.
USPC .............................................. 435/6.1; 435/7.1

(58) Field of Classification Search
None
See application file for complete search history.

(56) References Cited

U.S. PATENT DOCUMENTS

| | | | |
|---|---|---|---|
| 6,297,051 | B1 | 10/2001 | Zavada et al. |
| 7,378,091 | B2 | 5/2008 | Gudas |
| 2004/0146955 | A1 | 7/2004 | Supuran |
| 2008/0095707 | A1 | 4/2008 | Supuran |
| 2010/0143247 | A1 | 6/2010 | Fenske et al. |

OTHER PUBLICATIONS

Eckhardt et al (Molecular Cancer Research, 2005. vol. 3, No. 1, pp. 1-13).*
Shibata et al (Cancer Gene Therapy, 2008. vol. 15, pp. 776-786).*
Ellsworth et al (Clinical Experimental Metastasis, 2009. vol. 26, pp. 205-213).*
Collins et al (Vascular Pharmacology, 2006. vol. 45, pp. 258-267).*
Chambers, et al., "Dissemination and growth of cancer cells in metastatic sites", Nature Reviews Cancer, vol. 2 No. 8, Aug. 2002, pp. 563-572.
Ramaswamy et al., "A molecular signature of metastasis in primary solid tumors", Nature Genetics, vol. 33 (1), Jan. 2003, pp. 49-54.
Van 'T Veer et al., "Gene expression profiling predicts clinical outcome of breast cancer", Nature, vol. 415, Jan. 31, 2002, pp. 530-536.
Van De Vijver et al., "A gene-expression signature as a predictor of survival in breast cancer", The New England Journal of Medicine, vol. 347 (25), Dec. 19, 2002, pp. 1999-2009.
Wang et al., "Gene-expression profiles to predict distant metastasis of lymph-node-negative primary breast cancer", Lancet, vol. 365 Feb. 19, 2005, pp. 671-679.
Nguyen et al., "Metastasis: from dissemination to organ-specific colonization", Nature Reviews Cancer, vol. 9 (4), Apr. 2009, pp. 274-284.
Gupta et al., "Mediators of vascular remodelling co-opted for sequential steps in lung metastasis", Nature, vol. 446, Apr. 12, 2007, pp. 765-770.
Minn et al., "Genes that mediate breast cancer metastasis to lung", Nature, vol. 436, Jul. 28, 2005, pp. 518-524.
Eckhardt et al., "Genomic analysis of a spontaneous model of breast cancer metastasis to bone reveals a role for the extracellular matrix", Mol Cancer Research, vol. 3(1), Jan. 2005, pp. 1-13.
Aslakson et al., "Selective events in the metastatic process defined by analysis of the sequential dissemination of subpopulations of a mouse mammary tumor", Cancer Research, vol. 52 No. 6, Mar. 15, 1992, pp. 1399-1405.
Lou et al., "Epithelial-mesenchymal transition (EMT) is not sufficient for spontaneous murine breast cancer metastasis", Developmental Dyamics, vol. 237 (10), accepted Jun. 10, 2008, published 2008, pp. 2755-2768.
Kroemer et al., "Tumor cell metabolism: cancer's Achilles heel", Cancer Cell, vol. 13 (6), Jun. 2008, pp. 472-482.
Chiche et al., "Hypoxia-inducible carbonic anhydrase IX and XII promote tumor cell growth by counteracting acidosis through the regulation of the intracellular pH", Cancer Research, vol. 69 (1), Jan. 1, 2009, pp. 358-368.
Achen et al., "Focus on lymphangiogenesis in tumor metastasis", Cancer Cell, vol. 7, No. 2, Feb. 2005, pp. 121-127.
Alitalo et al., "Lymphangiogenesis in development and human disease", Nature, vol. 438, Dec. 15, 2005, pp. 946-953.
Tavazoie et al., "Endogenous human microRNAs that suppress breast cancer metastasis", Nature, vol. 451, Jan. 10, 2008, pp. 147-152.
Ghellal et al., "Prognostic significance of TGF beta 1 and TGF beta 3 in human breast carcinoma", Anticancer Research, vol. 20 (6B), accepted Oct. 23, 2000, published 2000, pp. 4413-4418.
Pastorekova et al., "Molecular mechanisms of carbonic anhydrase IX-mediated pH regulation under hypoxia", BJU International, vol. 101, Supplement 4, Jun. 2008, pp. 8-15.
Gatenby et al., "A microenvironmental model of carcinogenesis", Nature Rev Cancer, vol. 8 (1), Jan. 2008, pp. 56-61.
Supuran, "Carbonic anhydrases: novel therapeutic applications for inhibitors and activators", Nature Reviews Drug Discov, vol. 7 (2), Feb. 2008, pp. 168-181.

(Continued)

*Primary Examiner* — Celine Qian
(74) *Attorney, Agent, or Firm* — Drinker Biddle & Reath LLP

(57) ABSTRACT

There is provided a method for determining tumour metastatic potential using biomarkers of tumour metastasis comprising any two of carbonic anhydrase-9 (CAIX), vascular endothelial growth factor C (VEGF-C), ephrin A5 (EFNA5), eph receptor B2 (EPHB2), transforming growth factor beta 3 (TGF-β3), pyruvate dehydrogenase kinase isoenzyme-3 (PDK3), carbonic anhydrase-12 (CAXII), keratin 14 (KRT14), hypoxia inducible factor 1 alpha subunit (HIF-1α), and tenascin C (TNC). CAIX, VEGF-C, EFNA5, EPHB2, TGF-β3 or PDK3 may be indicators of moderate metastatic potential, while CAXII, KRT14, HIF-1α, or TNC may be indicators of high metastatic potential. The biomarkers may be used to assess malignancies or cancers having hypoxic regions, such as breast cancer.

8 Claims, 9 Drawing Sheets

(56) References Cited

OTHER PUBLICATIONS

Choi, et al., "Expression of carbonic anhydrase IX is associated with postoperative recurrence and poor prognosis in surgically treated oral squamous cell carcinoma", Human Pathology, vol. 39 (9), accepted Oct. 25, 2007, published 2008, pp. 1317-1322.

Kon-No et al., "Carbonic anhydrase IX expression is associated with tumor progression and a poor prognosis of lung adenocarcinoma", Lung Cancer, vol. 54 (3), accepted Aug. 29, 2006, published 2006, pp. 409-418.

Tan et al., "The key hypoxia regulated gene CAIX is upregulated in basal-like breast tumours and is associated with resistance to chemotherapy", British Journal of Cancer, vol. 100 (2), accepted Nov. 11, 2008, published 2009, pp. 405-411.

Chia et al., "Prognostic significance of a novel hypoxia-regulated marker, carbonic anhydrase IX, in invasive breast carcinoma", Journal of Clinical Oncology, vol. 19, No. 16, Aug. 15, 2001, pp. 3660-3668.

Mazzone et al, "Heterozygous deficiency of PHD2 restores tumor oxygenation and inhibits metastasis via endothelial normalization", Cell, vol. 136 (5), Mar. 6, 2009, pp. 839-851.

Galluzzo et al., "Prevention of hypoxia by myoglobin expression in human tumor cells promotes differentiation and inhibits metastasis", The Journal of Clinical Investigation, vol. 119 (4), Apr. 1, 2009, pp. 1-11.

Ebos et al., "Accelerated metastasis after short-term treatment with a potent inhibitor of tumor angiogenesis", Cancer Cell, vol. 15 (3), Mar. 3, 2009, pp. 232-239.

Paez-Ribes et al., "Antiangiogenic therapy elicits malignant progression of tumors to increased local invasion and distant metastasis", Cancer Cell, vol. 15 (3), Mar. 3, 2009, pp. 220-231.

Reynolds et al., "Stimulation of tumor growth and angiogenesis by low concentrations of RGD-mimetic integrin inhibitors", Nature Medicine, vol. 15, No. 4, Apr. 2009, pp. 392-400.

Loges et al., "Silencing or fueling metastasis with VEGF inhibitors: antiangiogenesis revisited", Cancer Cell, vol. 15 (3), Mar. 3, 2009, pp. 167-170.

Potter et al., "Diagnostic, prognostic and therapeutic implications of carbonic anhydrases in cancer", British Journal of Cancer, vol. 89 (1), accepted Mar. 4, 2003, published 2003, pp. 2-7.

Lal et al., "Transcriptional response to hypoxia in human tumors", Journal of the National Cancer Institute, vol. 93, No. 17, Sep. 5, 2001, pp. 1337-1343.

Wykoff et al., "Hypoxia-inducible expression of tumor-associated carbonic anhydrases", Cancer Research, vol. 60, Dec. 15, 2000, pp. 7075-7083.

Svastova et al., "Hypoxia activates the capacity of tumor-associated carbonic anhydrase IX to acidify extracellular pH", FEBS Letters, vol. 577 (3), available online Oct. 28, 2004, pp. 439-445.

McPHEE et al., "Integrin-linked kinase regulates E-cadherin expression through PARP-1", Developmental Dynamics, vol. 237 (10), accepted Jun. 25, 2008, published 2008, pp. 2737-2747.

Silvia et al., "Carbonic anhydrase IX (CA IX) as a potential target for cancer therapy", Cancer Therapy, vol. 2, electronically published Jul. 2004, pp. 245-262.

Brennan et al., "CA IX is and Independent Prognostic Marker in Premenopausal Breast Cancer Patients with One to Three Positive Lymph Nodes and a Putative Marker of Radiation Resistance", Clinical Cancer Research, vol. 12(21), Nov. 1, 2006, pp. 6421-6431.

Klatte et al., "Molecular Signatures of Localized Clear Cell Renal Cell Carcinoma to Predict Disease-Free Survival after Nephrectomy", Cancer Epidemiology, Biomarkers & Prevention, published online Feb. 24, 2009, vol. 18, No. 3, pp. 894-900.

Proescholdt et al., "Expression of hypoxia-inducible carbnoic anhydrases in brain tumors", Neuro-Oncology, Oct. 2005, vol. 7, pp. 465-475.

Yates et al., "X:Map: annotation and visualization of genome structure for Affymetrix exon array analysis", Nucleic Acids Research, published online Oct. 11, 2007, vol. 36, pp. D780-786.

Generali, et al., "Role of carbonic anhydrase IX expression in prediction of the efficacy and outcome of primary epirubicin/tamoxifen therapy for breast cancer", *Endocrine-Related Cancer* (2006) 13 921-930.

\* cited by examiner a

67NR 67NR hCA IX b

☐ Normoxia ■ Hypoxia ▨ Hypoxia + CAI17

Human CA IX negative

Human CA IX positive

BIOMARKERS OF CANCER METASTASIS

CROSS REFERENCE TO RELATED APPLICATIONS

This application is a Divisional of U.S. application Ser. No. 12/795,269, filed on Jun. 7, 2010, which claims the benefit of priority of U.S. Provisional Patent Application No. 61/184,380 filed on Jun. 5, 2009, the content of which is incorporated herein by reference in its entirety.

FIELD OF THE INVENTION

The present disclosure relates generally to diagnostic techniques for cancer. More particularly, the present disclosure relates to biomarkers of cancer metastasis.

BACKGROUND OF THE INVENTION

Metastasis, the primary cause of cancer mortality is a complex process with multiple steps that include tumour cell invasion, intravasation, extravasation, and establishment of secondary tumours in distant organs[1]. For breast cancer, genomic analysis of primary tumours and metastases from patients has identified sets of genes whose expression appear to be prognostic of outcome[2-4]. In addition, this type of analysis has led to sub-classification of human breast cancers into intrinsic subtypes that can also predict outcome and therapeutic response[2-5]. Despite this significant progress, the functions of genes within these classifications, and whether they are drivers of tumour progression or simply bystander markers, remains unclear. Furthermore, the molecular properties of primary tumours that dictate metastatic potential versus those that do not, have not been defined.

For breast cancer, several potential candidate metastasis genes have been identified for organ-specific metastasis to the bone, lungs and brain[6]. For lung metastasis, the collective expression of genes such as epiregulin, MMP-1 and -2, and Cox-2[7], have been found to be causative in promoting metastasis. CAIX has also been implicated in breast cancer.

For instance, U.S. Pat. No. 6,297,051 discloses that abnormal expression of CAIX may signal oncogenesis, and accompanying diagnostic and prognostic methods. Therapeutics targeted to the CAIX gene or protein are contemplated.

U.S. Patent Publication 2004/0146955 discloses methods for inhibiting the growth of preneoplastic and neoplastic vertebrate cells with abnormal expression of carbonic anhydrase-9 (CAIX). Specific CAIX inhibitors are disclosed.

Pastorekov & Z'vada (*Cancer Therapy* 2, 245-262 (2004)) suggest CAIX as a therapeutic target for cancer treatment.

Brenna, D. J. et al. (*Clinical Cancer Research* 12(21), 6421-6431 (2006)) disclose CAIX as a prognostic marker in premenopausal breast cancer patients.

U.S. Patent Publication 2008/0095707 discloses therapeutic methods for inhibiting the growth of neoplastic cells that abnormally express CAIX, for example, with CAIX inhibitors. Screening methods for identification of compounds which inhibit CAIX are contemplated.

U.S. Pat. No. 7,378,091 discloses monoclonal and polyclonal antibodies directed against CAIX which may be used in diagnosis or treatment of disorders associated with increased activity of CAIX, including cancers.

However, other genes which drive metastasis or dictate tumour grade (including metastatic potential) remain unknown. It would, therefore, be desirable to identify new or improved indicators of tumour metastatic potential. It would be advantageous to develop diagnostic or prognostic indicators capable of identifying tumours of moderate or high metastatic potential or of discriminating between tumours of differing metastatic potentials.

SUMMARY OF THE INVENTION

Generally, there is provided a panel for detecting biomarkers of tumour metastasis.

In a first aspect, there is provided a panel for detecting biomarkers of tumour metastasis. In one embodiment, there is provided a panel for detecting biomarkers of tumour metastasis, wherein said biomarkers comprise at least two of carbonic anhydrase-9 (CAIX), vascular endothelial growth factor C (VEGF-C), ephrin A5 (EFNA5), eph receptor B2 (EPHB2), transforming growth factor beta 3 (TGF-β3), or pyruvate dehydrogenase kinase isoenzyme-3 (PDK3), carbonic anhydrase-12 (CAXII), keratin 14 (KRT14), hypoxia inducible factor 1 alpha subunit (HIF-1α), or tenascin C (TNC).

In another aspect, there is provided a method of determining tumour metastatic potential. In one embodiment, the method comprises measuring expression levels in a tumour tissue sample of at least two indicators of metastatic potential which are each independently CAIX, VEGF-C, EFNA5, EPHB2, TGF-β3, PDK3, CAXII, KRT14, HIF-1α, or TNC; and comparing said expression levels to a control to determine metastatic potential.

In another aspect, there is provided a method of selecting cancer treatment. In one embodiment, the method comprises measuring expression levels in a tumour tissue sample of at least two indicators of metastatic potential which are each independently CAIX, VEGF-C, EFNA5, EPHB2, TGF-β3, PDK3, CAXII, KRT14, HIF-1α, or TNC; comparing said expression levels to a control to determine metastatic potential; and selecting an aggressive treatment regime if said tumour is determined to have metastatic potential.

In another aspect, there is provided a kit comprising the above-noted panel of biomarkers. In one embodiment, there is provided a kit comprising the panel for detecting biomarkers of tumour metastasis, wherein the biomarkers comprise at least two of CAIX, VEGF-C, EFNA5, EPHB2, TGF-β3, PDK3, CAXII, KRT14, HIF-1α, or TNC, and instructions for use.

In another aspect, there is provided a method of identifying or validating a putative cancer therapeutic. In one embodiment, the method comprises measuring expression levels of biomarkers comprising at least two of CAIX, VEGF-C, EFNA5, EPHB2, TGF-β3, PDK3, CAXII, KRT14, HIF-1α, or TNC in a sample of malignant cells; exposing said malignant cells to a putative cancer therapeutic; and identifying or validating said putative cancer therapeutic if said expression levels are reduced following exposure.

In one aspect, the biomarkers disclosed herein may be useful in determining tumour grade. In one embodiment, the biomarkers may be useful in discriminating tumours of low, moderate and high metastatic potential.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures wherein.

and low (67NR) metastatic potential pertinent to Example 1. Part a shows the data expressed as relative numerical values, with relative values corresponding to microarray hybridization data. Part b shows corresponding microarray expression analysis data.

Figure 2:
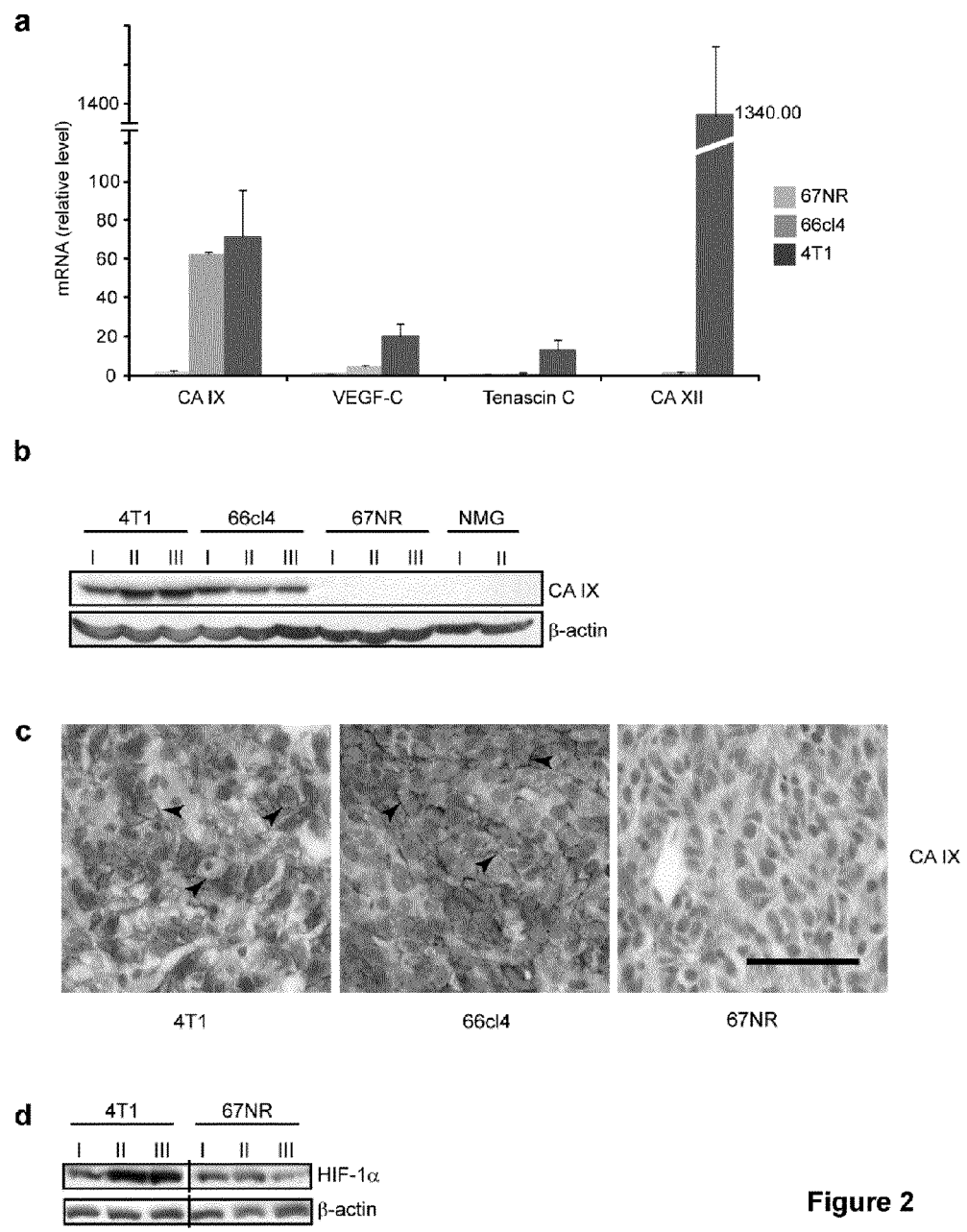

FIG. 2 provides expression results in an animal model of mammary tumours, and is pertinent to Example 1. Part a depicts quantitative RT-PCR validation of differential expression of certain biomarkers in 67NR, 66cl4 and 4T1 cells. Part b depicts expression analysis of CAIX protein in whole tissue extract from the indicated tumors (NMG indicates a normal mammary gland control). Part c depicts immunohistochemistry for CAIX on sections of primary tumours from the indicated cell lines, with prominent expression (dark regions) at the cell membrane indicated with arrowheads. Part d depicts Western blot analysis of H1F-1α expression in whole tissue extracts from cells of the indicated primary tumours, with β-actin used as a loading control.

Figure 3:
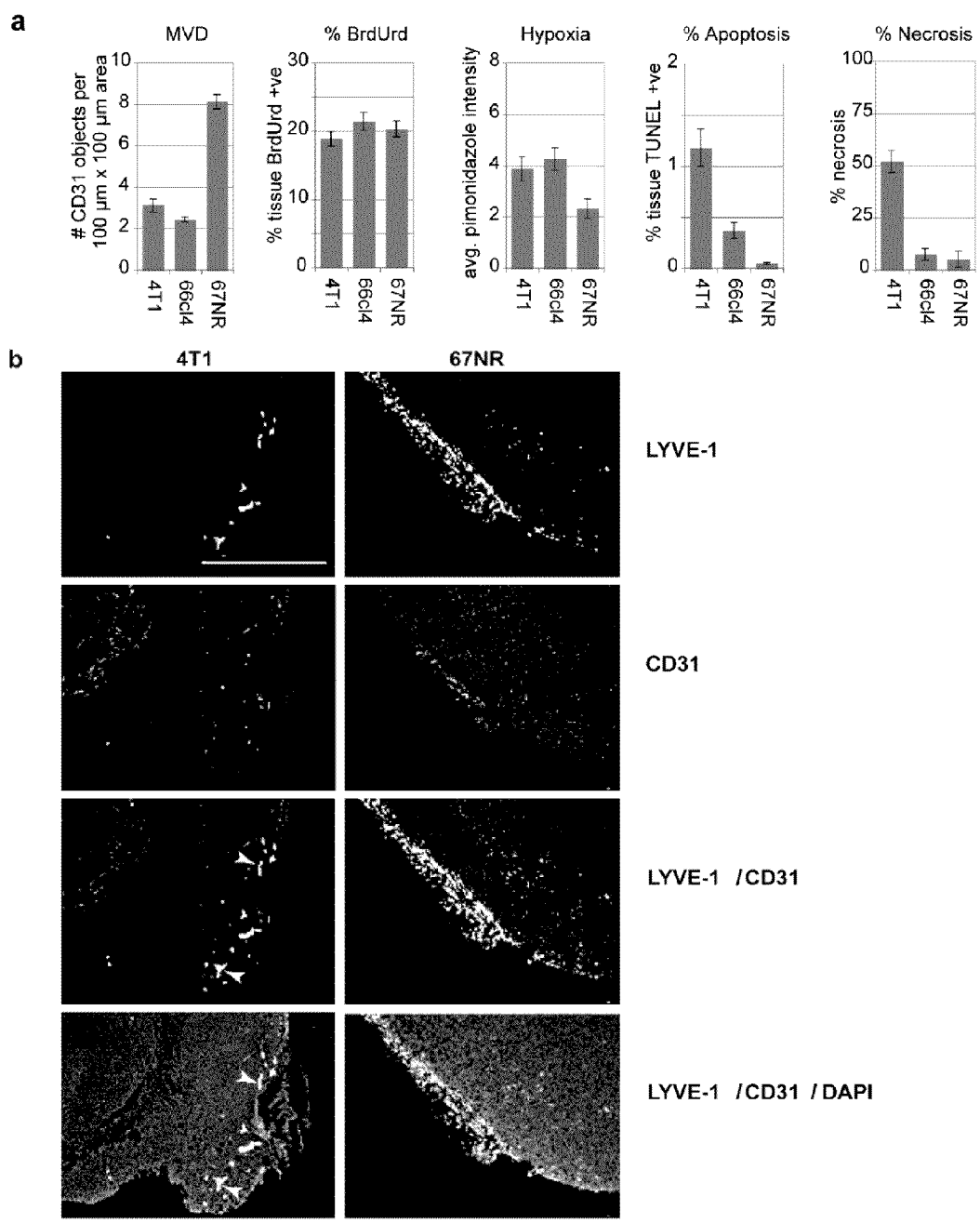

FIG. 3 depicts data regarding tumour architecture pertinent to Example 2. Part a depicts a comparison of microvessel density (MVD), proliferation, hypoxia, apoptosis, and necrosis across 4T1, 66cl4 and 67NR tumours. Part b depicts immunohistochemistry for LYVE-1 and CD31 on sections of primary tumours from the 4T1 and 67NR tumour models.

Figure 4:
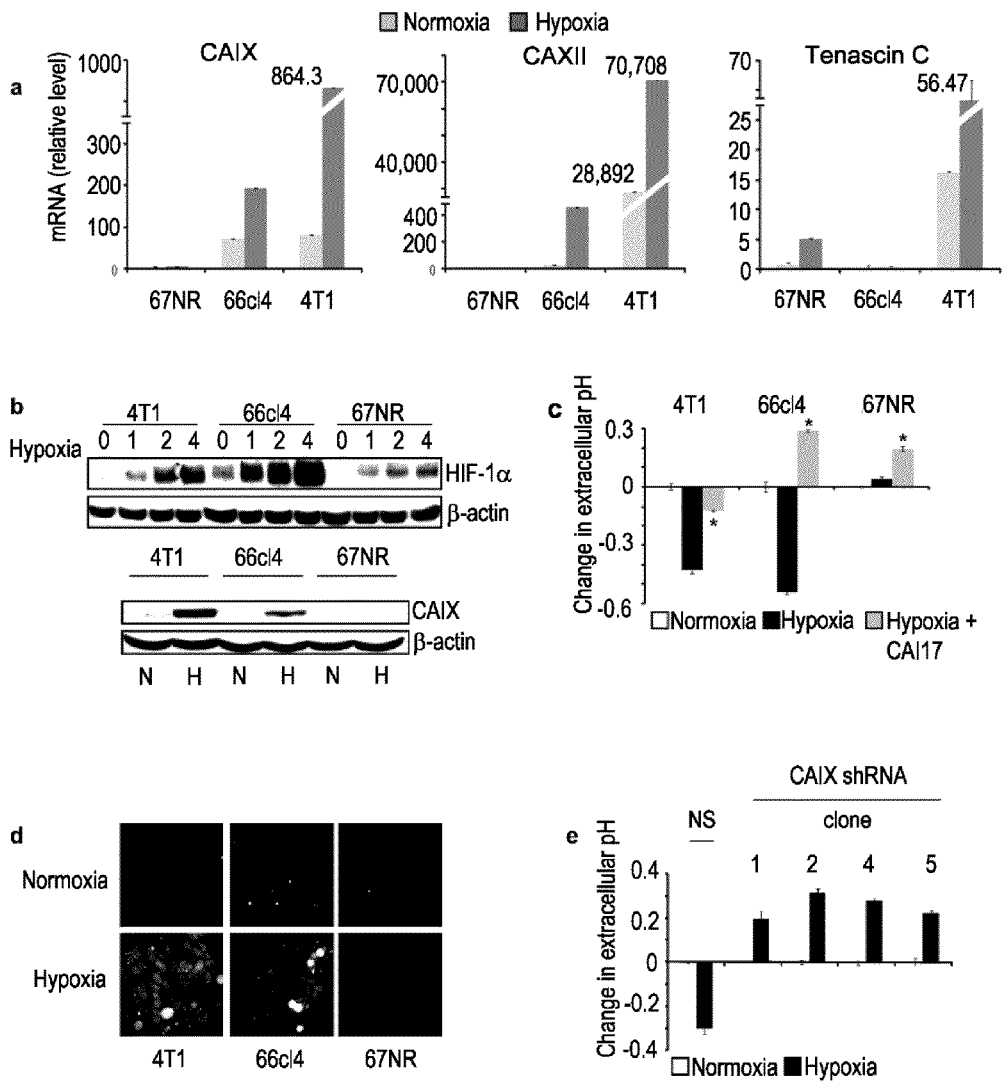

FIG. 4 depicts biomarker expression data pertinent to Example 3. Part a depicts expression levels of CAIX, CAXII and Tenascin C mRNA in cell lines 67NR, 66cl4 and 4T1. Part b depicts H1F-1α stabilization (top panel) and CAIX expression (bottom panel) in the indicated cell lines (4T1, 66cl4, and 67NR) under normoxic (N) and hypoxic (H) conditions, with β-actin used as a loading control. Part c depicts change in extracellular pH following culturing of the indicated cell lines under normoxia and hypoxia in the presence or absence of CAI 17. Part d depicts the extent of FITC-bound CAI 17 binding to 4T1, 66cl4 and 67NR cells under normoxia or hypoxia. Part e depicts change in extracellular pH for 4T1 cells transfected with non-silencing (NS) and CAIX-targeting shRNAs ("CA IX shRNA"; clones 1, 2, 4 and 5).

Figure 5:
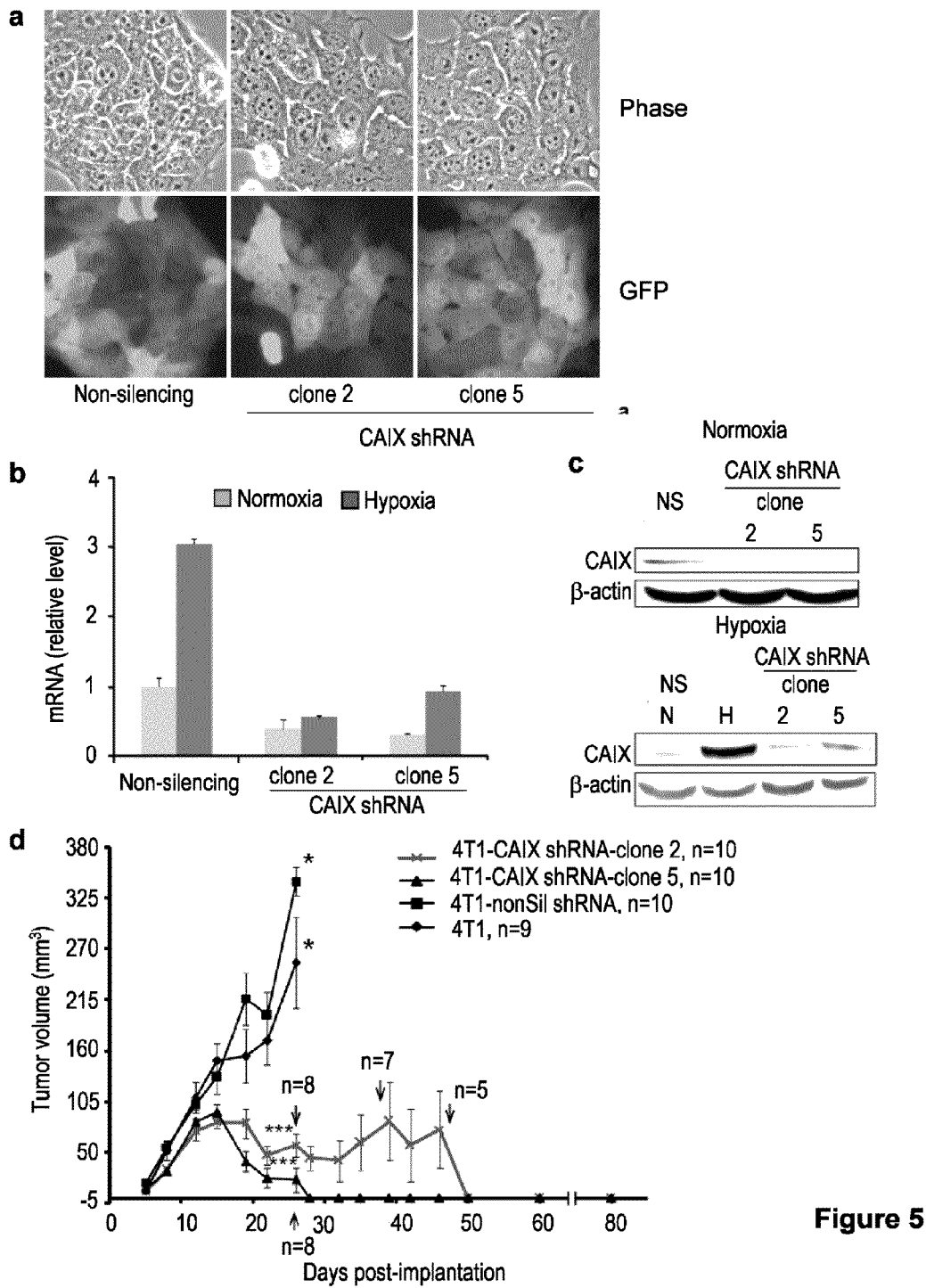

FIG. 5 depicts data on shRNA silencing of CAIX and its effects pertinent to Example 3. Part a depicts cellular expression of transfected GFP as a surrogate for transfection of a construct expressing shRNA directed against CAIX ("CA IX shRNA"). Part b depicts relative levels of CAIX mRNA expression in 4T1 cells expressing non-silencing (NS) or CAIX-targeted shRNAs (clones 2 and 5). Part c depicts CAIX protein expression in cells expressing non-silencing (NS) or CAIX-targeting shRNA ("CA IX shRNA"), with β-actin used as a loading control. Part d depicts plots showing tumour volume for parental 4T1 cells (circular data points), 4T1 cells expressing non-silencing (square data points) and two clones of 4T1 cells expressing CAIX-targeting shRNA (x-shaped data points for clone 2 and triangular data points for clone 5) over time.

Figure 6:
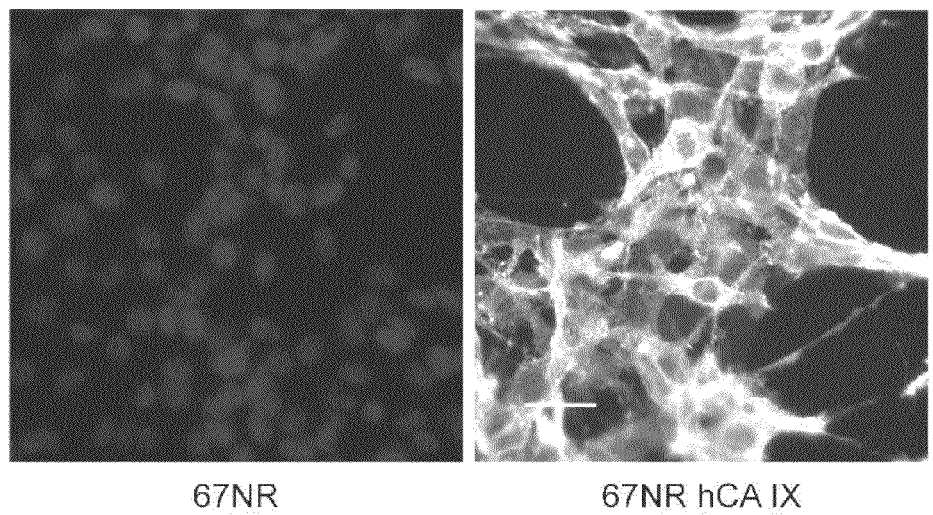
Figure 6:
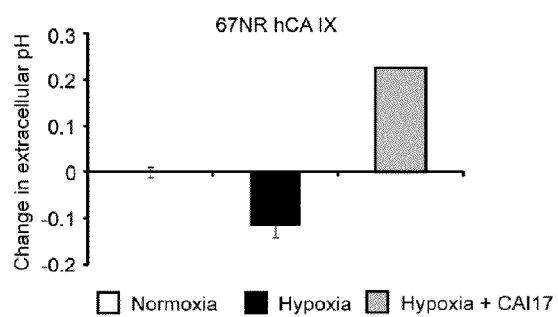

FIG. 6 depicts over-expression of human CAIX in cells of low metastatic potential and its effects, and is pertinent to Example 3. Part a depicts immunocytochemistry for human CAIX (hCAIX) in 67NR cells and 67NR cells expressing hCAIX ("67NR hCAIX"). Part b depicts change in pH of culture medium for 67NR cells expressing hCAIX under normoxic, hypoxic or hypoxic conditions with CAI 17.

Figure 7:
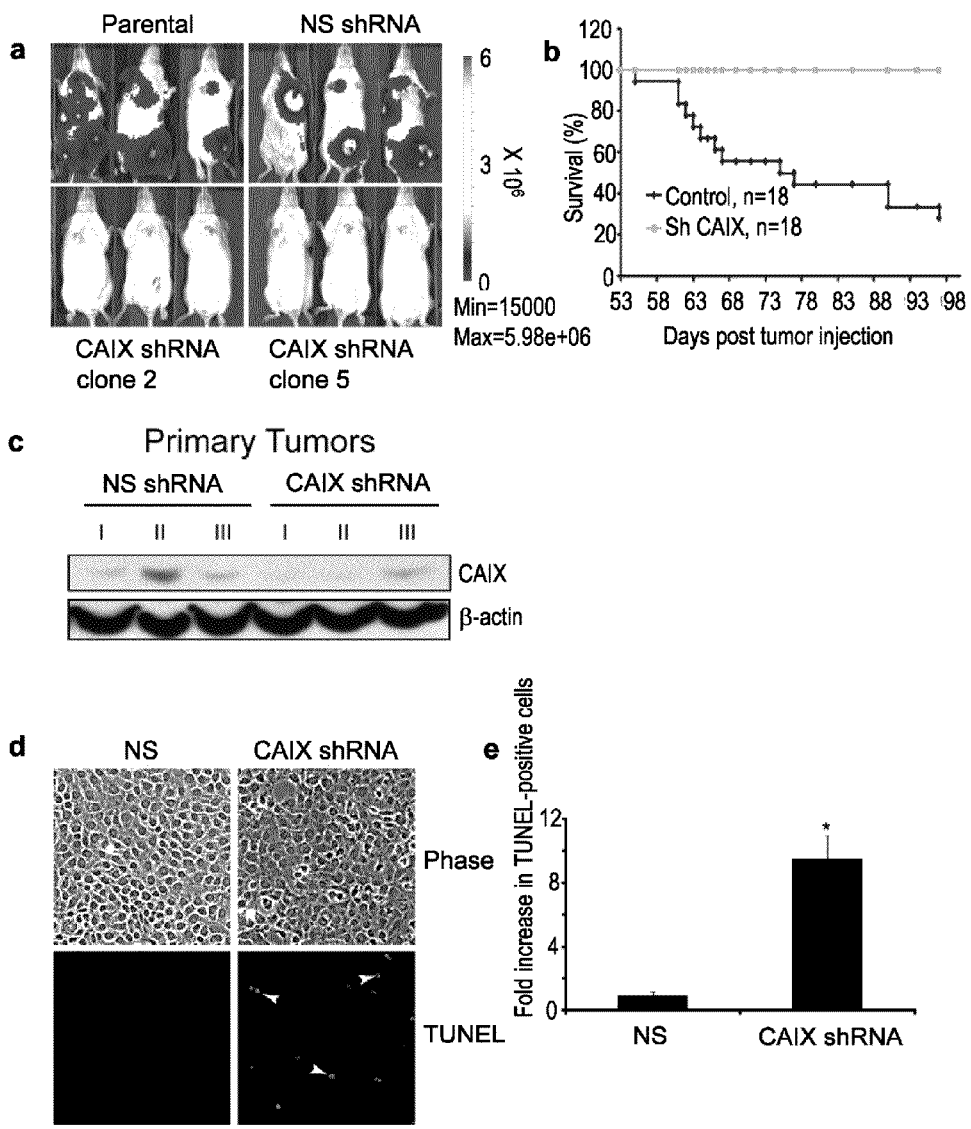

FIG. 7 depicts data on shRNA silencing of CAIX and effects on tumour growth and survival pertinent to Example 4. Part a depicts in vivo bioluminescent images of mice with primary and metastatic tumours derived from control breast cancer cells (parental and NS shRNA expressing cells) and two clones (clone 2 and clone 5) expressing shRNA directed to CAIX ("shCAIX"), with dark regions indicating expression and lighter regions within those dark regions indicative of even higher expression. Part b is a plot showing the percentage of mice surviving in each of two study arms comprising (a) pooled control (dark line) and (b) pooled shRNA targeting CAIX (lighter line) groups as a function of time. Part c depicts Western blot analysis of expression of CAIX in whole tissue extracts from primary tumours formed by parental 4T1 cells, and 4T1 cells expressing non-silencing ("NshRNA") shRNAs or shRNA targeted to CAIX ("CA IX shRNA"), with β-actin used as a loading control. Part d, shows apoptotic cells in 4T1 cells expressing non-silencing (NS) and CAIX-targeting shRNA ("CA IX shRNA"), with exemplary apoptotic cells indicated with arrowheads in the lower panels depicting TUNEL assay results. Part e shows quantified data pertaining to apoptosis for the cells expression non-silencing and CAIX-targeting shRNA.

Figure 8:
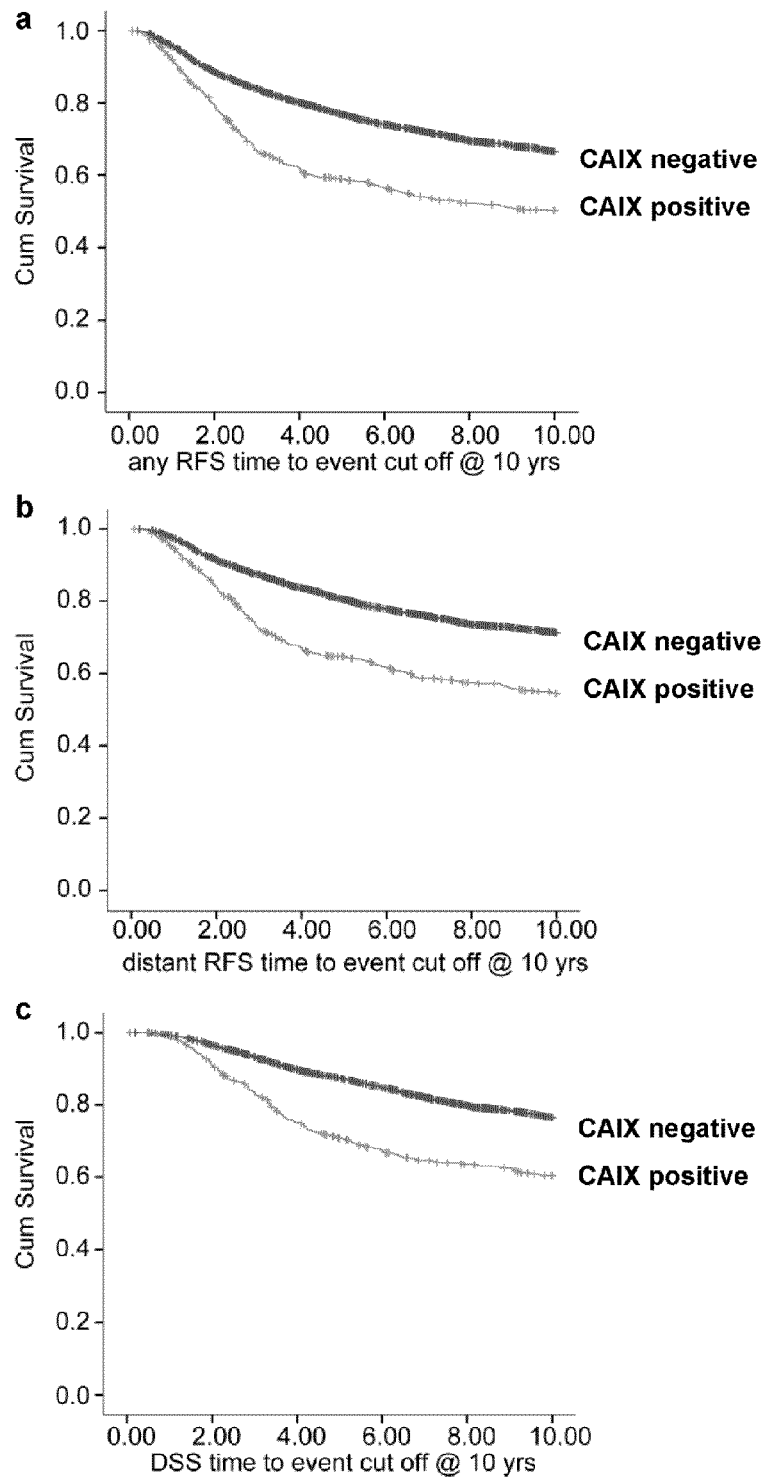

FIG. 8 depicts data pertaining to CAIX as a prognostic indicator, pertinent toe Example 5. Part a, depicts a Kaplan-Meier plot of cumulative survival ("Cum Survival") as a function of relapse-free survival time to event (cut off 10 years post cancer-diagnosis), with the CAIX positive group depicted as the light line and the CAIX negative group depicted as the dark line. Part b depicts a Kaplan-Meier plot of cumulate survival ("Cum Survival") as a function of survival time to distant metastatic event ("distant RFS"; cut off 10 years post cancer-diagnosis), with the CAIX positive group depicted as the light line and the CAIX negative group depicted as the dark line. Part c depicts a Kaplan-Meier plot of cumulate survival ("Cum Survival") as a function of overall survival time (cut off 10 years post cancer-diagnosis), with the CAIX positive group depicted as the light line and the CAIX negative group depicted as the dark line.

Figure 9:
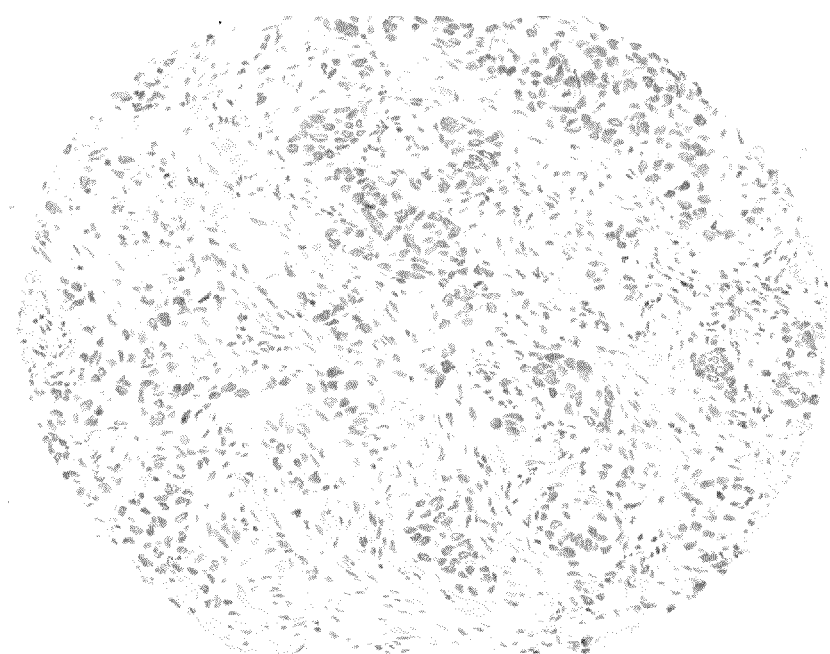
Figure 9:
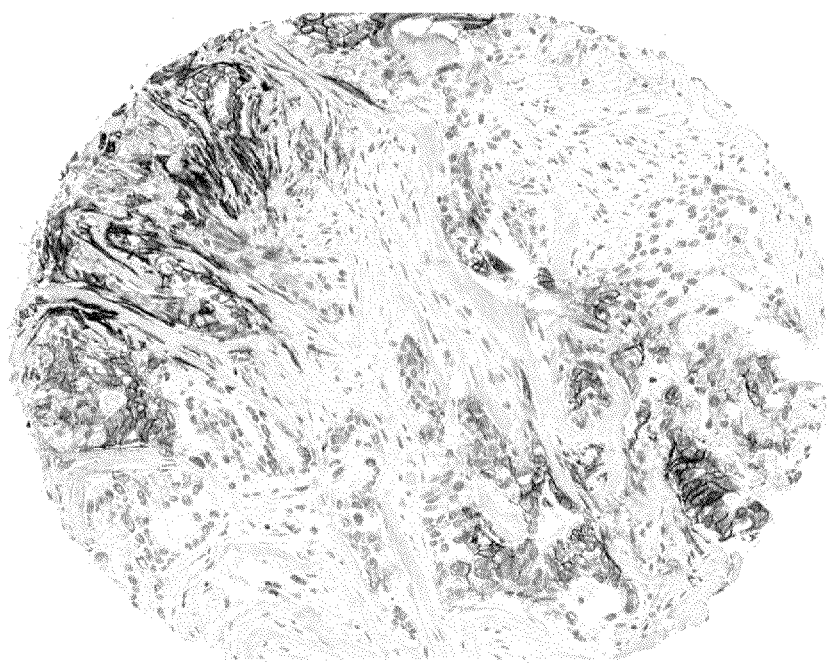

FIG. 9 is pertinent to Example 5 and depicts representative examples of CAIX negative and CAIX positive human breast cancer tissue cores from the tumour tissue microarray (TMA), with stained (dark) regions corresponding to CAIX expression in the CAIX positive sample.

DETAILED DESCRIPTION

There is provided a panel for detecting biomarkers useful, through a variety of methods that would be known to those skilled in the art, for determining the risk of cancer metastasis. Biomarkers of the invention may also have potential for use, for example, in predicting the treatment response of patients with or as novel targets enabling the development of new therapeutic agents for treatment of breast cancer. The biomarkers of some embodiments were discovered through whole transcriptome cDNA hybridization as transcripts differentially expressed in murine tumours with high, moderate, or low metastatic potential. Use of the panel in appropriate assays or methods including, in some embodiments, cDNA or oligonucleotide arrays or quantitative real-time RT-PCR-based techniques may enable identification of tumours with high metastatic potential.

Definitions

A "biomarker" is an organic biomolecule which is differentially present in a sample taken from a subject of one phenotypic status (e.g., having a disease) as compared with another phenotypic status (e.g., not having the disease or having a different sub-type, category, or severity of disease). A biomarker is differentially present between different phenotypic statuses if the mean or median expression level of the biomarker in the different groups is calculated to be statistically significant. Common tests for statistical significance would be known to a skilled person and include, among others, t-test, ANOVA, Kruskal-Wallis, Wilcoxon, Mann- Whitney and odds ratio. Biomarkers, alone or in combination, provide an indication or measure of relative risk that a subject belongs to one phenotypic status or another. As such, they may be useful as markers of disease presence, disease classification or sub-typing, predictors of disease outcome (prognostics), predictors of effective treatment, and markers of treatment efficacy (theranostics) and/or toxicity, etc. Biomarkers may also serve as therapeutic targets themselves in some instances.

A biomarker may encompass a gene (which may be coding and non-coding), including variants (e.g. due to normal population variation) or mutants thereof. A biomarker may also encompass an mRNA encoded by a gene, including variants (including splice variants and variants due to normal population variation) or mutants thereof, or a corresponding molecule such as a cDNA. A biomarker may also be a portion of a gene or an mRNA or a corresponding portion of a cDNA. A biomarker may also be a protein, including variants, mutants, isoforms (e.g. due to alternate splicing of exons), or a post-translational modification thereof. They may also comprise an immunogenic portion of a protein which may be detected, for example, with an antibody. As such, gene/protein names and symbols, as used herein, are (unless otherwise specified) intended to encompass corresponding genes, mRNA, cDNAs, proteins, variants, mutants, or fragments thereof, etc.

Specific genes referred to herein (e.g. carbonic anhydrase-9 (CAIX), carbonic anhydrase-12 (CAXII), vascular endothelial growth factor C (VEGF-C), ephrin A5 (EFNA5), eph receptor B2 (EPHB2), tenascin C (TNC), transforming growth factor beta 3 (TGF-β3), pyruvate dehydrogenase kinase isoenzyme-3 (PDK3), keratin 14 (KRT14), or hypoxia inducible factor 1 alpha subunit (HIF-1α)) are intended to encompass nucleic acid sequences or partial sequences encoding proteins having a polypeptide sequence corresponding to naturally occurring sequences as well as variant or homologous polypeptide sequences, fragments, analogies and derivatives having an activity at least substantially identical to a wild-type protein. Likewise, specific proteins referred to herein (e.g. CAIX, CAXII, VEGF-C, EFNA5, EPHB2, TNC, TGF-β3, PDK3, KRT14, and HIF-1α) are intended to encompass proteins and polypeptides having amino acid sequences corresponding to naturally occurring sequences, as well as variant or homologous polypeptide sequences, fragments and derivatives having an activity at least substantially identical to a wild-type protein. Specific sequences for genes and proteins referred to herein could be readily identified by a skilled person, for example, in gene and nucleic acid sequence databases available at the web site of the National Centre for Biotechnology Information (NCBI) web site, including GenBank.

A "biomarker signature", as used herein, indicates the expression of a set of biomarkers in a given sample.

The term "expression" is indicative of transcription of a gene to yield an mRNA (often termed "gene expression" or "mRNA expression") or translation of an mRNA to yield an encoded protein (often termed "protein expression"). As used herein, expression encompasses steady state expression. A skilled person would readily appreciate that measured expression levels will depend on factors such as, for example, transcription rate, translation rate, RNA stability, or protein stability, etc. Expression may also increase or decrease in response to one or more specific stimulus, and characteristic expression response patterns of biomarkers (and uses thereof) are fully contemplated herein.

Relative expression levels, as set out herein, are intended to be in comparison to an appropriate control sample. As stated below, in some instances, this may be a tissue or cells of low metastatic potential (e.g. 67NR) or a non-cancerous tissue sample (e.g., normal mammary gland, in some embodiments, in the case of breast cancer). Appropriate controls may be human samples, in some embodiments, such as characterized tumour samples from a tissue bank. As such, "normal expression", as recited herein, refers to expression which does not differ significantly from a control sample. "Increased expression" or "elevated expression" refers to an expression level which is greater than a control, while "decreased expression" or "reduced expression" refers to an expression level which is less than a control. In referring to expression for a particular group of biomarkers herein (including groups preceded by "all of"), a certain amount of experimental variation is to be expected. Recited relative expression is intended to refer to overall results, which may be averages or other statistical calculations based on assessing multiple genes and/or multiple data points, such as experimental replicates. Further, relative expression may be indicative of an expression pattern exhibited by a majority of tested biomarkers.

In measuring expression in a human sample, a skilled person would appreciate that the recited biomarkers refer, in such a context, to human genes or proteins. Likewise, when dealing with mouse or another species (e.g., vertebrates), a skilled person could readily identify the intended homologous gene(s), protein(s) and related sequences. In comparing expression levels measured in a human sample to those measured in a mouse sample (e.g. for comparisons of a human tumour to 67NR, 66cl4, or 4T1) a skilled person would appreciate that some differences in absolute expression levels may occur due to cross-species differences. What is important is whether the overall pattern of expression is relatively elevated, relatively similar, or relatively reduced compared to the standard or control.

The "panel" for detecting biomarkers would be understood to encompass means of detecting the biomarkers, including (in some embodiments) means of measuring expression levels of the biomarkers, or presence vs. absence. In the case in which the biomarker is a nucleic acid (DNA, mRNA, cDNA, etc.) the panel may encompass complementary nucleic acid molecules which specifically hybridize to the biomarker molecules under conditions appropriate to the specific assay which are widely known. The nucleic acids to be detected or the complementary nucleic acids (termed "probes") may be labeled, for example fluorescently or with a radioactive isotope. Synthetic probes may also be generated and encompass non-natural or modified nucleotides, such as locked nucleic acid (LNA) or peptide nucleic acid (PNA), for example. Suitable assays to detect nucleic acids may include (but are not limited to) microarrays (including cDNA- or oligonucleotide-based, for example), RNA hybridization (Northern blot, slot blot, or dot blot, for example), PCR (quantitative or real time RT-PCR, for example), or genotyping methods, including SNP genotyping methods (e.g. restriction fragment length polymorphism (RFLP), sequencing, primer extension, 5'-nuclease, or oligonucleotide ligase-based assays, for example), etc. When the biomarker is a protein, the panel may encompass antibodies (monoclonal or polyclonal), fragments thereof, or antigen-binding polypeptides capable of specifically binding to the intended target proteins. Suitable antibodies may, in some instances, be purchased or may be generated through known methods. Suitable assays for detecting the protein may encompass immunohistochemistry methods or immunoassays, such as an enzyme linked immunosorbent assay (ELISA).

The term "oligonucleotide" refers to a molecule comprised of two or more deoxyribonucleotides or ribonucleotides, usually more than ten. The exact size will depend on many factors, which, in turn, depend on the ultimate function or use of the oligonucleotide. In the context of an array, an oligonucleotide will be of sufficient length and sequence composition so as to permit specific hybridization of target sequences under standard array conditions, which would be known to a skilled person. Oligonucleotides may be generated in any manner, including chemical synthesis, DNA replication, reverse transcription, or a combination thereof. Oligonucleotide arrays are widely known in the art and are available commercially.

Similarly, "cDNA", as recited in the context of a "cDNA array" is intended to encompass full-length and partial cDNA sequences of sufficient length and sequence composition as to permit specific hybridization under standard array conditions which would be known to a skilled person. cDNAs may be generated through reverse transcriptase PCR (RT-PCR) of mRNA. Cloned cDNAs are available commercially.

The term "complementary" and "complementarity" refer to polynucleotides (i.e., a sequence of nucleotides) related by the base-pairing rules. For example, the sequence 5'-A-T-G-C-3' is complementary to the sequence 5'-G-C-A-T-3'. Complementarity may be "partial," in which case only some of the bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in PCR-based amplification reactions, as well as detection methods that depend upon binding between nucleic acids.

The term "polypeptide", as used herein, refers to a sequence of amino acid residues linked together by peptide bonds or modified peptide bonds. A polypeptide can be naturally occurring, recombinant, synthetic, or a combination of these. A polypeptide may be a fragment of a naturally occurring protein or polypeptide.

In assessing human tumour samples, relative expression could be determined by comparing expression to human tumours (or cell lines derived therefrom) of known high, moderate, or low metastatic potential, such as characterized tumours available in tissue banks.

"High metastatic potential", as set out herein, is indicative of a propensity to form distant metastasis or metastasis to multiple sites or organs. An example of a cell line with a high metastatic potential is the 4T1 cell line.

"Moderate metastatic potential", as set out herein, may be indicative of local, tissue specific, organ-specific, or site-specific metastasis. For example, in the case of the breast cancer cell line 66cl4, moderate metastatic potential indicates metastasis to the lung.

"Low metastatic potential", as set out herein, is indicative of a low rate of metastasizing or a non-metastatic tumour. Such behavior is exemplified by the NR67 cell line. Tumours with low metastatic potential may still pose significant medical problems in terms of growth of the primary tumour, etc.

An "expression vector", is used herein to express a specific gene in a target cell via the cellular-transcription and translation machinery. The vector is frequently a plasmid containing the cloned gene and appropriate regulatory sequences that act as enhancer and promoter regions and lead to efficient transcription and translation of the gene carried on the expression vector. The gene's open reading frame may be linked to an epitope tag to facilitate detection, for example, by Western blot. The plasmid may also contains markers such as a drug-resistance gene for selection or green fluorescent protein (GFP) to enable transfection efficiency to be determined. A gene or other sequence to be expressed, in conjunction with regulatory elements, is sometimes referred to as a "construct".

Panel for Detecting Biomarkers of Tumour Metastasis

In a first aspect, there is provided a panel for detecting biomarkers of tumour metastasis. In one embodiment, there is provided a panel for detecting biomarkers of tumour metastasis, wherein the biomarkers comprise at least two of carbonic anhydrase-9 (CAIX), vascular endothelial growth factor C (VEGF-C), ephrin A5 (EFNA5), eph receptor B2 (EPHB2), transforming growth factor beta 3 (TGF-β3), pyruvate dehydrogenase kinase isoenzyme-3 (PDK3), carbonic anhydrase-12 (CAXII), keratin 14 (KRT14), hypoxia inducible factor 1 alpha subunit (HIF-1α), or tenascin C (TNC).

In an exemplary embodiment, there is provided a panel for detecting biomarkers of tumour metastasis, wherein the biomarkers comprise at least one of CAIX, VEGF-C, EFNA5, EPHB2, TGF-β3, or PDK3; and at least one of CAXII, TNC, KRT14 or HIF-1α.

In an exemplary embodiment, at least one of CAIX, VEGF-C, EFNA5, EPHB2, TGF-β3, or PDK3 is an indicator of moderate metastatic potential, and at least one of CAXII, TNC, KRT14 or HIF-1α is an indicator of high metastatic potential. In such an embodiment, the panel may permit tumours of high, moderate, and low metastatic potential to be identified and/or discriminated.

In one embodiment, there is provided a panel for detecting biomarkers of tumour metastasis, wherein the biomarkers comprise at least one of CAIX, VEGF-C, TGF-β3; and at least one of TNC, KRT14, and CAXII. In an exemplary embodiment, there is provided a panel for detecting biomarkers of tumour metastasis, wherein the biomarkers comprise all of CAIX, VEGF-C, TGF-β3, TNC, KRT14, and CAXII.

In one embodiment, there is provided a panel for detecting biomarkers of tumour metastasis, wherein the biomarkers comprise at least one of CAIX, VEGF-C; and at least one of TNC, KRT14, and CAXII. In an exemplary embodiment, there is provided a panel for detecting biomarkers of tumour metastasis, wherein the biomarkers comprise all of CAIX, VEGF-C, TNC, KRT14, and CAXII.

In a further exemplary embodiment, there is provided a panel for detecting biomarkers of tumour metastasis, wherein the biomarkers comprise CAIX and CAXII. In one specific example, there is provided a panel for detecting biomarkers of tumour metastasis, wherein the biomarkers comprise CAIX and CAXII; and one or more of VEGF-C, EFNA5, EPHB2, TNC, TGF-β3, PDK3, KRT14, or HIF-1α.

Figure 1:
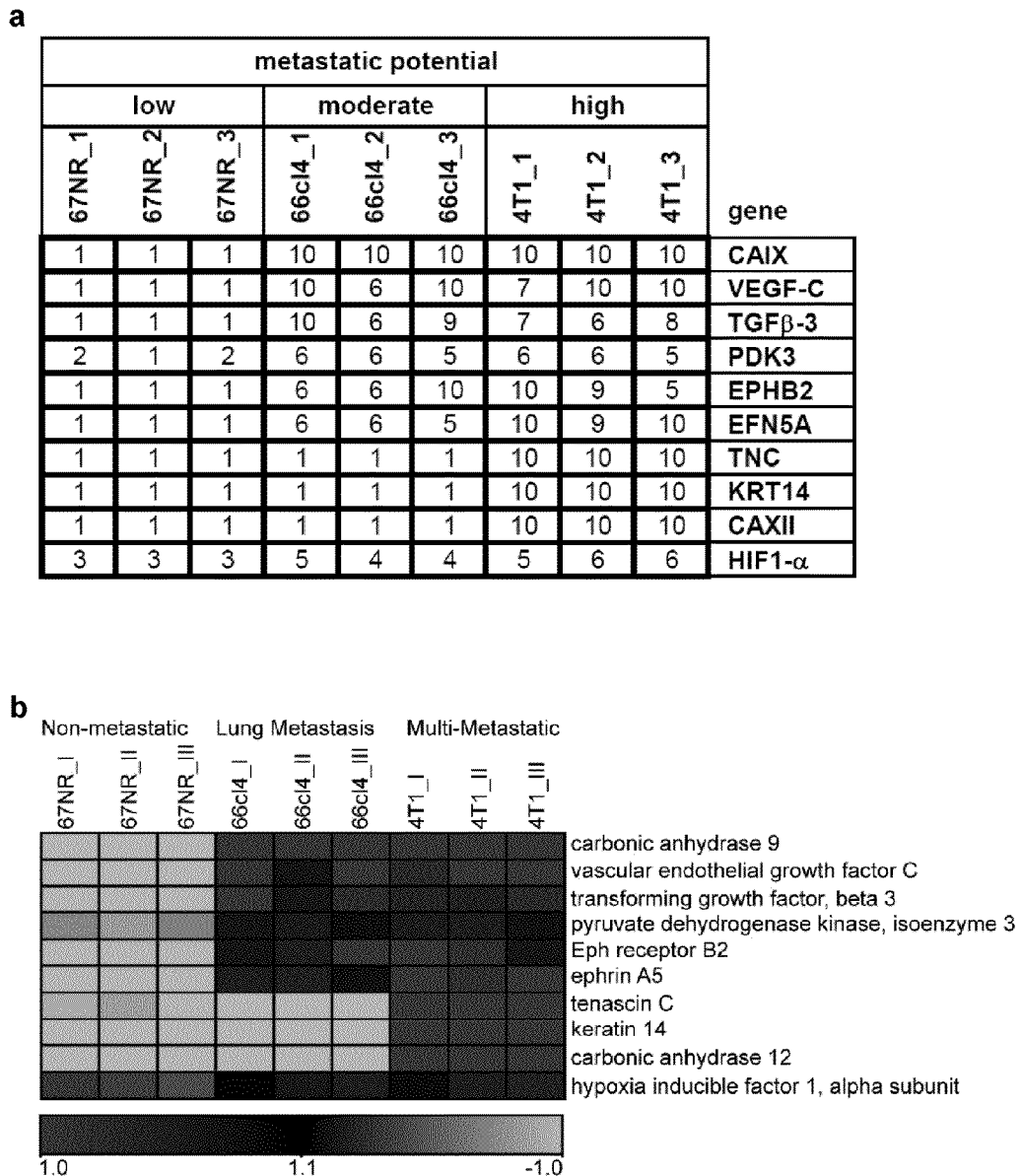
FIG. 1 depicts expression data for a panel of biomarkers in primary mammary tumours of high (4T1), moderate (66cl4)

As exemplified in FIG. 1, parts a and b, a specific example is a panel for detecting biomarkers of tumour metastasis, wherein the biomarkers comprise all of CAIX, CAXII, VEGF-C, EFNA5, EPHB2, TNC, TGF-β3, PDK3, KRT14, and HIF-1α. In one embodiment, the panel comprises a set of nucleic acid probes complementary to the 10 corresponding biomarker mRNAs. In another embodiment, the panel comprises a set of antibodies or antigen-binding polypeptides directed to said biomarkers. Testing expression levels with the complementary set of nucleic acid probes, antibodies, or antigen-binding polypeptides may provide a biomarker signature indicative of elevated risk of metastatic progression of a tumour. For example, it may permit tumours of high, moderate, and low metastatic potential to be distinguished.

In a further embodiment, there is provided a panel for detecting biomarkers of tumour metastasis, wherein the biomarkers comprise CAXII, TNC, KRT14 or HIF-1α which may be particularly useful in identifying tumours of high metastatic potential.

In certain embodiments, the panel is for diagnostics, tumour sub-typing, prognostics, or theranostics. In exemplary embodiments, the biomarkers may be used for detecting cancer, determining risk of metastasis, determining tumour grade, determining tumour sub-type, selecting optimized treatment, predicting the treatment response, measuring treatment response, predicting clinical outcome, predicting likelihood of recurrence, as targets enabling the development of new therapeutic agents for treatment of breast cancer, or as indicators for screening for candidate therapeutic agents.

In one embodiment, the tumour may be a primary tumour. In an exemplary embodiment, the tumour is a breast cancer tumour. A specific example is a human breast cancer tumour. In a further specific example, the panel may be used for predicting risk of tumour metastasis of human breast cancer.

Method of Determining Tumour Metastatic Potential

In another aspect, there is provided a method of determining tumour metastatic potential. In one embodiment, the method comprises measuring expression levels in a tumour tissue sample of at least two indicators of metastatic potential which are CAIX, VEGF-C, EFNA5, EPHB2, TGF-β3, PDK3, CAXII, KRT14, HIF-1α, or TNC; and comparing said expression levels to a control to determine metastatic potential.

In some embodiments, the at least two indicators of metastatic potential comprise CAIX and CAXII.

In some embodiments, the step of measuring expression levels comprises measuring protein or mRNA levels.

In some embodiments, the tumour tissue sample is from a human breast cancer tumour.

In some embodiments, the control comprises a control sample having low or no metastatic potential and said tumour is determined to have metastatic potential when said expression levels are elevated relative to said control.

In an exemplary embodiment, the method comprises measuring expression levels in a tumour tissue sample of at least one indicator of moderate metastatic potential which is CAIX, VEGF-C, EFN5, EPHB2, TGF-β3, or PDK3, and expression levels of at least one indicator of high metastatic potential which is CAXII, KRT14, HIF-1α or TNC; comparing said expression levels to a control; and determining (a) low metastatic potential if expression levels of said at least one indicator of moderate metastatic potential and said at least one indicator of high metastatic potential are both less than or substantially equal to said control, (b) moderate metastatic potential if said expression levels of said at least one indicator of moderate metastatic potential are elevated compared to said control, and said expression levels of said at least one indicator of high metastatic potential are less than or equal to said control, or (c) a high metastatic potential if said expression levels of said at least one indicator of moderate metastatic potential and said at least one indicator of high metastatic potential are elevated compared to said control.

In one embodiment, the at least one indicator of moderate metastatic potential is at least one of CAIX, VEGF-C, or TGF-β3 while the at least one indicator of high metastatic potential is at least one of TNC, KRT14, or CAXII. In an exemplary embodiment, the at least one indicator of moderate metastatic potential comprises all of CAIX, VEGF-C, and TGF-β3 while the indicator of high metastatic potential metastasis comprises all of TNC, KRT14, and CAXII.

In one embodiment, the at least one indicator of moderate metastatic potential is at least one of CAIX or VEGF-C while the at least one indicator of high metastatic potential is at least one of TNC, KRT14, or CAXII. In an exemplary embodiment, the at least one indicator of moderate metastatic potential may comprise both of CAIX and VEGF-C while the at least one indicator of high metastatic potential comprises all of TNC, KRT14, and CAXII.

In one embodiment, the at least one indicator of moderate metastatic potential is CAIX and the indicator of high metastatic potential metastasis is CAXII. In an exemplary embodiment, the method comprises measuring expression levels of CAIX and CAXII together with at least one or more of VEGF-C, EFNA5, EPHB2, TNC, TGF-β3, PDK3, KRT14, or HIF-1α.

In a specific example, as illustrated in FIG. 1, parts a and b, the method comprises measuring expression levels of all of CAIX, CAXII, VEGF-C, EFNA5, EPHB2, TNC, TGF-β3, PDK3, KRT14, and HIF-1α.

In one embodiment CAXII, TNC, KRT14, or HIF-1α may be used to identify tumour of high metastatic potential. In an exemplary embodiment, CAXII, TNC, KRT14, and HIF-1α may be used to this end. In a further exemplary embodiment, CAXII, TNC, and KRT14 may be used to identify tumours of high metastatic potential.

In some embodiments, the tumour tissue sample may be obtained from a patient. In others, it may be obtained from a biopsy or a tissue bank, for example.

In some embodiments, biomarker may be assayed by measuring corresponding mRNA expression levels. mRNA expression levels may be measured by a wide variety of techniques which would be known to a skilled person and are exemplified (but not limited to) reverse-transcriptase PCR (RT-PCR) or real time RT-PCR, a cDNA-based array, an oligonucleotide array, or a Northern blot hybridization.

In an exemplary embodiment, cDNAs corresponding to the above-noted biomarkers are spotted on a solid support to form a cDNA microarray. Changes in the transcriptome (specifically in expression levels of biomarker mRNAs) of breast tumours or tissue indicative of malignant transformation are then detected by hybridizing total RNA (or corresponding sample cDNA) isolated from test cells or clinical specimens (cancerous or normal, for example) to the cDNA microarray and detecting the strength of the hybridisation signal at specific spots (addresses) on the microarray. Test sample (e.g. tumour tissue) results may be compared to controls samples (such as, for example, a non-malignant tissue such as normal mammary gland, or a tumour of low metastatic potential such as 67NR).

In another exemplary embodiment, the expression levels of biomarkers may be interrogated or quantified using a quantitative real-time reverse-transcriptase PCR (q-RT-PCR) approach to specifically amplify and detect the expression of the mRNAs with the appropriately-designed probe or primer sets. Current state of the art qRT-PCR-based technologies allow simultaneous high-throughput amplification and detection of any transcript one can design specific probes or primers to in a single experiment with minimal sample requirements. One advantage of the qRT-PCR multiplex microfluidics card approach (relative to expression arrays for example) is that RNA from formalin-fixed paraffin-embedded (FFPE) archival specimens may be used and one is not limited to sourcing RNA from fresh-frozen specimens. Alternative methodologies for measuring expression of transcript sequences disclosed in this specification are contemplated and within the scope of the invention. These may include but are not limited to expression analysis microarray-based platforms or technologies, such as those offered by Affymetrix Inc.

In some embodiments, biomarkers may be assayed by measuring corresponding protein expression levels. These may be measured by a wide variety of techniques which would be known to a skilled person. In an exemplary embodiment, expression of the biomarkers of the invention may be measured in cells, tissues, or cellular extracts by immunohistochemical techniques employing immunoglobulins or antibodies specific or selective to protein epitopes of the biomarkers as the detection reagents. Specific polyclonal and/or monoclonal antibodies to biomarkers of the invention may be generated by standard methods and may be used to assess expression by methods exemplified (but not limited to) by an ELISA (enzyme-linked immunosorbent assay), an immunohistochemical assay, a Western blot assay or a mass spectrometry assay. Tissue sections may also be stained for protein expression using standard techniques.

In one embodiment, tumors may be imaged utilizing labeled antibodies directed to corresponding proteins of the above-described biomarkers. This may be performed on tissue or biopsy samples. In an exemplary embodiment, tumor may be imaged in vivo by utilizing labeled antibodies to corresponding proteins of the above-described biomarkers. In a further exemplary embodiment, hypoxic regions of a tumor may be imaged as indicated above.

The biomarkers disclosed herein are also contemplated to encompass or be interrogated through the use of common polymorphisms, such as single nucleotide polymorphisms (SNPs) in corresponding genomic, mRNA, or cDNA (and corresponding variation in protein sequences, if applicable). A skilled person would readily be able to identify such polymorphisms on the basis of data held, for example, in the databases of the National Centre for Biotechnology Information, such as GenBank and the single nucleotide polymorphism database (dbSNP) database, etc.

For measurement of mRNA or protein expression levels, or for assessing related polymorphisms, a skilled person would appreciate that the resulting biomarkers expression profile may be compared to that of an appropriate control. In some embodiments, this control may be from tissue or cells with low or no metastatic potential. The control may be a tumor with low or no metastatic potential. A specific example is 67NR cells or tumours derived therefrom. In certain embodiments, the control may be from a relevant non-cancerous sample, which may be, in certain cases, taken from the individual with cancer whose tumour is being assessed. A specific example is normal mammary gland tissue.

In one specific example, high metastatic potential is exemplified by an expression profile similar to that exhibited by 4T1 cells (see FIG. 1, parts a and b). In another specific example, moderate metastatic potential is exemplified by an expression profile similar to that exhibited by 66cl4 cells (see FIG. 1, parts a and b) may be indicative of moderate metastatic potential. In a further specific example, low metastatic potential is exemplified by an expression profile similar to that exhibited by NR67 cells (see FIG. 1, parts a and b).

In certain embodiments, the determination of risk of tumour metastatic potential may correlated with other variables. For example, information regarding biomarker profile and risk of tumour metastasis may be used to detect cancer, determine risk of metastasis, determine tumour grade, determine tumour sub-type, select optimized treatment, predict the treatment response, measure treatment response, predict clinical outcome, predict likelihood of recurrence, select therapeutic target(s) enabling the development of new therapeutic agents for treatment of breast cancer, or to screen for efficacy of a candidate therapeutic agent. In an exemplary embodiment, the biomarkers are useful in assessing these variables in solid tumors or malignancies having hypoxic compartments or regions.

A specific example is the correlation of biomarker CAIX with survival time parameters, as set out in Example 5 below.

Method of Selecting Treatment

In another aspect, there is provided a method of selecting cancer treatment.

In one embodiment, the method comprises carrying out the above-described method of determining tumour metastatic potential; and selecting an aggressive cancer treatment if said tumour is determined to have metastatic potential.

For example, the method may comprise measuring expression levels in a tumour tissue sample of at least two indicators of metastatic potential which are CAIX, VEGF-C, EFNA5, EPHB2, TGF-β3, PDK3, CAXII, KRT14, HIF-1α, or TNC; comparing said expression levels to a control to determine metastatic potential; and selecting an aggressive cancer treatment if said tumour is determined to have metastatic potential.

In an exemplary embodiment, the method comprises measuring expression levels in a tumour tissue sample of at least one indicator of moderate metastatic potential which is CAIX, VEGF-C, EFN5, EPHB2, TGF-β3, PDK3, and expression levels of at least one indicator of high metastatic potential which is CAXII, KRT14, HIF-1α or TNC; comparing said expression levels to a control; and determining (a) low metastatic potential if expression levels of said at least one indicator of moderate metastatic potential and said at least one indicator of high metastatic potential are both less than or substantially equal to said control, (b) moderate metastatic potential if said expression levels of said at least one indicator of moderate metastatic potential are elevated compared to said control, and said expression levels of said at least one indicator of high metastatic potential are less than or equal to said control, or (c) a high metastatic potential if said expression levels of said at least one indicator of moderate metastatic potential and said at least one indicator of high metastatic potential are elevated compared to said control; and then (a) selecting a highly aggressive treatment regime if said tumour is determined to have high metastatic potential, (b) selecting a moderately aggressive treatment regime if said tumour is determined to have moderate metastatic potential, or (c) selecting a non-aggressive or less aggressive treatment regime if said tumour is determined to have low metastatic potential.

For example, the method may comprise measuring expression levels in a tumour tissue sample of at least one indicator of moderate metastatic potential which is CAIX, VEGF-C, EFN5, EPHB2, TGF-β3, PDK3, and expression levels of at least one indicator of high metastatic potential which is CAXII, KRT14, HIF-1α or TNC; comparing said expression levels to a control; and determining (a) selecting a non-aggressive or less aggressive treatment regime if expression levels of said at least one indicator of moderate metastatic potential and said at least one indicator of high metastatic potential are both less than or substantially equal to said control, (b) selecting a moderately aggressive treatment regime if said expression levels of said at least one indicator of moderate metastatic potential are elevated compared to said control, and said expression levels of said at least one indicator of high metastatic potential are less than or equal to said control, or (c) selecting a highly aggressive treatment regime if said expression levels of said at least one indicator of moderate metastatic potential and said at least one indicator of high metastatic potential are elevated compared to said control.

In some embodiments, the step of measuring may comprise measuring expression levels of at least one of CAIX, VEGF-C, TGF-β3; and at least one of TNC, KRT14, and CAXII. In an exemplary embodiment, the step of measuring may comprise measuring expression levels of all of CAIX, VEGF-C, TGF-β3, TNC, KRT14, and CAXII.

In some embodiments, the step of measuring may comprise measuring expression levels of at least one of CAIX, VEGF-C; and at least one of TNC, KRT14, and CAXII. In an exemplary embodiment, the step of measuring may comprise measuring expression levels of all of CAIX, VEGF-C, TNC, KRT14, and CAXII.

In an exemplary embodiment, the step of measuring may comprise measuring expression levels of CAIX and CAXII. In one specific example, the step of measuring may comprise measuring expression levels of CAIX and CAXII together with at least one or more of VEGF-C, EFNA5, EPHB2, TNC, TGF-β3, PDK3, KRT14, or HIF-1α.

In a specific example, the step of measuring may comprise measuring expression levels of all of CAIX, VEGF-C, EFN5, EPHB2, TGF-β3, PDK3, CAXII, KRT14, HIF-1α and TNC.

In certain embodiments, an appropriate highly aggressive treatment regime may comprise treatments which would be known to a skilled person, such as surgical intervention, chemotherapy, radiation therapy, adjuvant therapy, hormone therapy, or close clinical surveillance, etc. A highly aggressive treatment regime may comprise proactive treatment to reduce or prevent metastasis, including distant or multiple metastases.

In some embodiments, a moderately aggressive treatment regime may also comprise surgical intervention, chemotherapy, radiation therapy, adjuvant therapy, hormone therapy, or close clinical surveillance, etc. It may also comprise proactive treatment to reduce or prevent local, organ-specific, tissue specific, or site-specific metastasis. In the case of breast cancer, this may include, in some embodiments, proactive treatment of or surveillance for metastasis to the lung.

In certain embodiments, suitable non-aggressive or less aggressive treatments would be known to a skilled person and may include conventional treatments listed above, but may also assume a lower likelihood of metastasis, with treatment focused on the primary tumour, for example.

In another embodiment, the biomarkers or corresponding genes, mRNAs or proteins are useful as therapeutic targets enabling development of novel agents for treatment of breast cancer. In exemplary embodiments, drugs, small molecules, antibodies, shRNAs or siRNAs, etc. may be employed (alone or in combination) to target biomarkers exhibiting increased expression or the cellular pathways in which their corresponding proteins function.

In another exemplary embodiment, the selected treatment regimen may comprise siRNAs or shRNAs which may be used to reduced or "knock down" expression of one or more biomarkers exhibiting increased expression. A specific example would be a highly aggressive treatment regime or a moderately aggressive treatment regime comprising an inhibitor of at least one indicator of moderate metastatic potential or an inhibitor of an indicator of high metastatic potential.

In one embodiment, the highly aggressive treatment regime or the moderately aggressive treatment regime comprise an inhibitor of the at least one indicator of moderate metastatic potential or of the at least one indicator of high metastatic potential.

In one embodiment, the highly aggressive treatment regime or the moderately aggressive treatment regime comprises an inhibitor of CAIX or CAXII. In some instances, CAIX or CAXII may serve a therapeutic target for tumours in which the genes are found to be up-regulated, individually or together. In other instances, they may served as therapeutic targets even if one or both gene exhibits normal expression. In some embodiments shRNA (see Example 4 below) or siRNA directed against CAIX may be used to treat tumours having metastatic potential. In a further exemplary embodiment, an aggressive treatment regime may comprises an inhibitor of CAIX, such as a small molecule or an antibody. A specific example is the use of the CAIX inhibitor, compound 17 (CAI 17). Thus, other suitable inhibitors, in some embodiments, may have an activity similar to CAI 17. In another embodiment, CAXII may be targeted with an siRNA, an shRNA, an antibody, a small molecule, or an inhibitor, etc.

In an exemplary embodiment, both CAIX and CAXII may serve as therapeutic targets in an aggressive treatment regimen. A specific example would be a highly aggressive treatment regime or a moderately aggressive treatment regime comprising an inhibitor CAIX and an inhibitor of CAXII.

Kits

In another aspect, there is provided a kit comprising the above-described panel for detecting biomarkers, and instructions for use.

In one embodiment, the kit comprises a panel for detecting biomarkers of tumour metastasis, wherein the biomarkers comprise at least two of CAIX, VEGF-C, EFNA5, EPHB2, TGF-β3, PDK3, CAXII, KRT14, HIF-1α, or TNC.

In an exemplary embodiment, the kit a panel for detecting biomarkers of tumour metastasis, wherein the biomarkers comprise at least one of CAIX, VEGF-C, EFNA5, EPHB2, TGF-β3, or PDK3; and at least one of CAXII, TNC, KRT14 or HIF-1α.

In one embodiment, the kit comprises a panel for detecting biomarkers of tumour metastasis, wherein the biomarkers comprise at least one of CAIX, VEGF-C, TGF-β3; and at least one of TNC, KRT14, and CAXII. In an exemplary embodiment, the kit comprises a panel for detecting biomarkers of tumour metastasis, wherein the biomarkers comprise all of CAIX, VEGF-C, TGF-β3, TNC, KRT14, and CAXII.

In one embodiment, the kit comprises a panel for detecting biomarkers of tumour metastasis, wherein the biomarkers comprise at least one of CAIX, VEGF-C; and at least one of TNC, KRT14, and CAXII. In an exemplary embodiment, the kit comprises a panel for detecting biomarkers of tumour metastasis, wherein the biomarkers comprise all of CAIX, VEGF-C, TNC, KRT14, and CAXII.

In a further exemplary embodiment, the kit comprises a panel for detecting biomarkers of tumour metastasis, wherein the biomarkers comprise CAIX and CAXII. In one specific example, the kit comprises a panel for detecting biomarkers of tumour metastasis, wherein the biomarkers comprise CAIX and CAXII; and one or more of VEGF-C, EFNA5, EPHB2, TNC, TGF-β3, PDK3, KRT14, or HIF-1α.

A specific example is the kit comprising a panel for detecting biomarkers of tumour metastasis, wherein the biomarkers comprise CAIX, CAXII, VEGF-C, EFNA5, EPHB2, TNC, TGF-β3, PDK3, KRT14, and HIF-1α.

In one embodiment, the kit comprises a antibodies, antigen-binding, or complementary nucleic acids for said biomarkers. The kit may comprise probes or assays for detecting expression of mRNA, cDNA or protein corresponding to the biomarkers. Suitable probes or assays may include complementary nucleic acids (including cDNA or oligonucleotides, for example) or antibodies, fragments thereof, or antigen-binding polypeptides directed against (i.e. capable of binding) the corresponding biomarker proteins.

In one embodiment, there is provided the kit comprising nucleic acid probes complementary to the 10 expressed nucleic acid sequences (mRNAs or cDNAs) corresponding to the biomarkers. In a further embodiment, there is provided a kit comprising antibodies or antigen-binding fragments for detecting the 10 corresponding biomarker proteins.

In a further embodiment the kit comprises a panel for detecting biomarkers of tumour metastasis, wherein the biomarkers comprise CAXII, TNC, KRT14 or HIF-1α which may be useful in identifying tumours of high metastatic potential.

The kit may include instructions for use in detecting cancer, determining risk of metastasis, determining tumour grade, determining tumour sub-type, selecting optimized treatment, predicting the treatment response, measuring treatment response, predicting clinical outcome, predicting likelihood of recurrence, as targets enabling the development of new therapeutic agents for treatment of breast cancer, or as indicators for screening for candidate therapeutic agents. In a specific example, the kit may be useful in predicting metastatic potential of a breast cancer tumour.

The instructions may indicates that at least one of CAIX, VEGF-C, EFNA5, EPHB2, TGF-β3, or PDK3 is an indicator of moderate metastatic potential while at least one of CAXII, TNC, KRT14 or HIF-1α is an indicator of high metastatic potential.

Method of Identifying or Validating a Putative Cancer Therapeutic

In another aspect, the above biomarkers may be used in a method of identifying or validating a putative cancer therapeutic.

In one embodiment, the method comprises measuring expression levels of the above-described biomarkers in a sample of malignant cells; exposing said malignant cells to said putative cancer therapeutic; and identifying or validating a putative cancer therapeutic if said expression levels are reduced following exposure.

In an exemplary embodiment, a first sample of malignant cells may be obtained and said expression levels may be measured. Said cells may then be exposed to a putative cancer therapeutic prior to a second sample being taken. Expression levels may be measured in the second sample. A cancer therapeutic may be identified or validated if expression levels are reduced in the second sample are reduced compared to said first sample. Alternatively, identification or validation may take place if the expression levels in said second sample are more similar to a control.

Suitable malignant cells may be derived from a tumour or malignancy in an organism or tissue bank, or may be cultured cells.

It is envisaged that such an assay as described above, by way of example, could be scaled up and used as a high throughput means of identifying or validating putative therapeutics on a large scale.

A skilled person would appreciate that a therapeutic so "identified" or "validated" would, in this context, require further testing in cell culture, animal models, or clinical trials, for example, to confirm activity or clinical utility.

In one embodiment, the biomarkers comprise at least two of CAIX, VEGF-C, EFNA5, EPHB2, TGF-β3, PDK3, CAXII, KRT14, HIF-1α, or TNC.

In an exemplary embodiment, the biomarkers comprise at least one of CAIX, VEGF-C, EFNA5, EPHB2, TGF-β3, or PDK3; and at least one of CAXII, TNC, KRT14 or HIF-1α.

In one embodiment, the biomarkers comprise at least one of CAIX, VEGF-C, TGF-β3; and at least one of TNC, KRT14, and CAXII. In an exemplary embodiment, the biomarkers comprise all of CAIX, VEGF-C, TGF-β3, TNC, KRT14, and CAXII.

In one embodiment, the biomarkers comprise at least one of CAIX, VEGF-C; and at least one of TNC, KRT14, and CAXII. In an exemplary embodiment, the biomarkers comprise all of CAIX, VEGF-C, TNC, KRT14, and CAXII.

In a further exemplary embodiment, the biomarkers comprise CAIX and CAXII. In one specific example, the biomarkers comprise CAIX and CAXII; and one or more of VEGF-C, EFNA5, EPHB2, TNC, TGF-β3, PDK3, KRT14, or HIF-1α.

As exemplified in FIG. 1, parts a and b, the biomarkers comprise all of CAIX, CAXII, VEGF-C, EFNA5, EPHB2, TNC, TGF-β3, PDK3, KRT14, and HIF-1α.

EXAMPLES

Unless otherwise stated, the following methods, techniques and reagents were used in the Examples which follow. Other standard techniques would be known to a skilled person.

Cell Culture and Hypoxic Exposure

The acquisition, generation and culture of the mouse breast cancer cell lines 4T1, 66cl4 and 67NR have been described previously[11]. These 3 cell lines stably express a luciferase reporter[11] and were cultured routinely in DMEM supplemented with 10% FBS, non-essential amino acids and 3 μg/ml puromycin. Incubation in normoxia was carried out in a humidified atmosphere of 5% $CO_2$ and 95% air at 37° C. Cells were maintained in conditions of hypoxia (1% $O_2$ and 5% $CO_2$ balanced with $N_2$) at 37° C. in a humidified incubator positioned in a sealed anaerobic workstation.

Generation of Knockdown Cells shRNAmir vectors targeting mouse CAIX and a non-silencing sequence were purchased from Open Biosystems (Huntsville, Ala.). Cells were grown to 90% confluence and transfected with the shRNAmir constructs using LipofectAMINE (Invitrogen Life Technologies) with the addition of the PLUS reagent (Invitrogen Life Techologies) according to the manufacturer's instructions. Previous selection of the transfected cells with puromycin precluded the use of this marker. Transfected cells were selected using hygromycin. For hygromycin-selected cells transfected with CAIX, stable clones were derived by limit dilution cloning using GFP as a screening tool. Transfected cell lines were grown routinely in the presence of puromycin and hygromycin. Suppression of CAIX expression was confirmed in normoxic and hypoxic conditions by qRT-PCR and Western blot.

Measurement of Extracellular pH

Cells were plated in 60 mm dishes and allowed to recover for 24 hours. Growth medium was then replaced with a standard 3 ml volume of fresh media and cells were incubated in normoxia or hypoxia for 72 hours. Spent media was collected in 15 ml conical tubes, maintained at 37° C. and pH was measured immediately using a digital pH meter. Triplicate plates were run for each condition and results were averaged. Cell layers were kept on ice and were harvested for qRT-PCR and Western blot analysis.

Pharmacological Inhibitors

CAI 17 was a generous gift from Dr. Claudiu Supuran (University of Florence, Florence, Italy). The chemical properties of this sulfonamide have been previously described[20,34]. The sulfonamide was dissolved in 100% DMSO, stored at −80° C. and diluted into culture medium just prior to application. Subconfluent cell monolayers were incubated with CAI 17 for 72 hours in normoxia or hypoxia, washed 3× in PBS and imaged using a Ziess Axioplan epifluorescence microscope.

Analysis of mRNA and Protein Expression

Quantitative Real-Time PCR (Q-RT-PCR) was conducted in 384-well plate on an Applied Biosystems (Foster City, Calif., USA) Q-RT-PCR instrument using Roche Universal Probe Library (UPL) (Roche Applied Science, Laval, Quebec, Canada) according to the manufacturer's instructions. Briefly 1 µg of total RNA from either subconfluent cells or snap frozen tissue was used in a 40 µl reaction to make cDNA. Subsequently, 10 µl of Q-RT-PCR mixture containing 100 nM UPL probe, 200 nM of each primer and TaqMan PCR master mix (Applied Biosystems) was loaded into each well. After a preliminary 95° C. incubation the samples were read for 40 cycles (95° C.: 30 sec, 60° C.: 30 sec, 72° C.: 60 sec). The values for mRNA expression were normalized using β-actin and/or GAPDH as the housekeeping genes. All Q-RT-PCR primers were designed using the Roche Applied Science online assay design centre for UPL system and were purchased from Invitrogen (Burlington, ON, Canada)[35]. Relative gene expression quantification data were acquired and analysed using an ABI Prism 7900HT Sequence detection System (Applied Biosystems) and using the standard $2^{-\Delta\Delta ct}$ method.

For immunoblotting cells or flash frozen tumour tissue were lysed in 1% Triton X-100 buffer (50 mM Hepes, pH=7.5, 150 mM NaCl, 10% glycerol, 1 mM EGTA and 2 mM EDTA), supplemented with 1 mM of each $Na_3OV_4$ and PMSF, 2 mM of NaF, and complete protease inhibitor cocktail (Roche). Protein concentrations were determined using the BCA Protein Assay (Pierce, Rockford, Ill., USA) according to the manufacturer recommendations. To enhance the detection of HIF-1α before degradation cells plated at equal densities were directly lysed in 4×SDS loading buffer. Western blots were performed using the following antibodies: mouse CA-9 (1:500), HIF-1α (1:250), human CAIX (1:1000) all from R&D systems, β-actin (1:10,000, Sigma) as a loading control.

Tumorigenesis and Spontaneous Metastasis Analysis

All animal procedures were done in accordance with protocols approved by the Institution Animal Care Committee at the BC Cancer research Centre and the University of British Columbia (Vancouver, BC). Briefly BALB/c (7-9 weeks old) female mice were orthotopically injected with 1×10⁶ viable single cells into the fourth mammary gland as previously described[11]. Primary tumour growth rates were recorded twice per week and calculated by applying calliper measurements into the modified ellipsoid formula $(L \times W^2)/2$. Tumour formation and metastasis progression was monitored and quantified using non-invasive in vivo bioluminescent imaging as previously described[11]. Mice were monitored daily and survival was followed for 80 days.

Immunohistochemistry 2 h before tumour excision mice were injected i.p. with BrdUrd as a 30-mg/mL solution in saline at 1500 mg/kg (Sigma) and Pimonidazole (Chemicon) at 60 mg/kg. DiOC₇(3) (70 µl, 0.6 mg/ml; Molecular Probes) in PBS were injected i.v. 5 min before tumour harvest. Serial tumour cryosections (10 µm thick) were cut with a Cryostar HM560 (Microm International), air-dried for 24 h, and imaged for DiOC₇(3) tissue fluorescence to visualize blood flow. Sections were fixed in 50% (v/v) acetone/methanol for 10 min at room temperature. Vasculature was stained using anti-PECAM/CD31 antibody (1:2000 clone, 2H8) and fluorescent Alexa 647 anti-hamster secondary (1:200, Invitrogen). Hypoxia was detected via bound pimonidazole adducts using polyclonal rabbit-anti-pimonidazole (1:2000) and an Alexa 488 anti-rabbit secondary (1:200, Molecular Probes). Apoptosis was detected using a TUNEL kit (Roche Diagnostics) with a TMR red tagged dUTP. Slides were imaged for fluorescence and then transferred to distilled water for 10 min and then treated with 2 M HCl at room temperature for 1 hour followed by neutralization for 5 min in 0.1 M sodium borate. Slides were then washed in distilled water and transferred to a PBS bath. Subsequent steps were each followed by a 5 min wash in PBS. DNA incorporated BrdUrd was detected using monoclonal rat anti-BrdUrd (1:500, clone BU1/75, Sigma) followed by an anti-mouse peroxidase conjugate antibody (1:200, Sigma) and a metal enhanced DAB substrate (1:10, Pierce). Slides were counterstained with haematoxylin, dehydrated and mounted using Permount (Fisher Scientific) before imaging.

For lymphangiogenesis the frozen sections were fixed with 2% PFA for 20 min, rinsed twice with PBS and then stained with rabbit anti-LYVE-1 (1:100) and rat anti-CD31 (1:100) dissolved in PBS containing 10% bovine serum albumin and 2% goat serum for 1 h at room temperature in a humidified container. Alexa 488 anti-rabbit and Alexa 546 anti-rat antibodies were used as secondary antibodies for 1 h followed by Vectashield mounting medium (Vector Laboratories) containing DAPI nuclear counter stain for mounting.

Image Acquisition The imaging system consists of a robotic fluorescence microscope (Zeiss Axioimager Z1, Oberkochen, Germany), a cooled, monochrome CCD camera (Retiga 4000R, QImaging, Vancouver, BC, Canada), a motorized slide loader and x-y stage (Ludl Electronic Products, Hawthorne, N.Y., USA) and customized ImageJ software (public domain program developed at the U.S. National Institutes of Health, available at the internet web site thereof, running on a Macintosh computer (Apple, Cupertino, Calif., USA). The system allows tiling of adjacent microscope fields of view. Using this system, images of entire tumour cryosections 1-2 cm² were be captured at a resolution of 0.75 µm/pixel.

Image Analysis for BrdUrd & TUNEL Mapping

Using NIH-Image and user supplied algorithms, images of CD31 fluorescence and BrdUrd, TUNEL or pimonidazole staining from each tumour section were overlaid and areas of necrosis and staining artifacts manually removed. On the fluorescence image, CD31 positive regions were identified by selecting all pixels 15 standard deviations above the tissue background levels. CD31 positive regions that were less than 5 µm² in size were considered artifacts and automatically removed from the analysis. BrdUrd and positive staining was identified by selecting pixels that were 5 standard deviations above tissue background levels. Measuring the distance from each point in the tissue to the nearest CD31 positive object and noting if it is BrdUrd positive or negative was used to determine the relation between proliferation and distance to the nearest blood vessel. The data was tabulated so as to determine the fraction of BrdUrd positive pixels of the total number pixels found at each distance to a blood vessel. Analysis of TUNEL and pimonidazole profiles were carried out in a similar fashion but using average signal intensity as a function of distance to the nearest vessel rather than the fraction of tissue above threshold.

Image Analysis for Tissue Parameters

Overall BrdUrd positive staining and average TUNEL or pimonidazole intensity was calculated from images of entire tumour sections following removal of necrotic regions and tissue artifacts (folds, tears, debris etc). Percent necrosis was calculated from the fraction of each tissue section that exhibited confluent necrosis.

Cell Proliferation and Apoptosis Assay

TUNEL labeling (Roche Applied Science) was employed for analysis of apoptosis according to the manufacturer's instructions with minor modifications. Briefly, subconfluent cells grown on coverslips were incubated for 48 h under normoxia or hypoxia in 1% serum, air-dried, fixed in 4% paraformaldehyde for 60 minutes and permeabilized for 10 min in PBS+0.1% Triton-X-100 held at room temperature. Cell layers were then incubated with the TUNEL reagents for 60 min at 37° C., washed in PBS and counterstained with a 1:10 000 dilution of H33342.

Statistical Analysis

Results were subjected to statistical analysis using the Data Analysis ToolPack in Excel software. Two-tailed p values were calculated using student's t-test. Data were considered significant for p<0.05.

Example 1

Differential Expression of Hypoxia Inducible Genes in Metastatic Versus Non-Metastatic Primary Tumours The complex nature of metastasis requires animal models that can recapitulate the human situation, including spontaneous metastasis from primary tumours and an intact immune system. A well established clinically relevant syngeneic mouse model of spontaneous breast cancer metastasis was used to investigate differential expression of hypoxia inducible genes in metastatic versus non-metastatic primary tumours[9,10]. The model is highly robust in that several syngeneic tumour cell lines with a spectrum of metastatic phenotypes have been isolated from a spontaneous metastatic mammary tumour in a BALB/cfC3H mouse. When injected into the mammary glands of mice, the tumour cell lines form primary tumours within two weeks[10,11], but vary in their metastatic potential and organ specificity. The 67NR cells are non-metastatic, whereas the 66cl4 produce spontaneous metastases to the lungs only, and the 4T1 are highly metastatic with spontaneous metastasis to several organs including lung[10,11]. Stable luciferase expressing cell lines have been engineered to monitor tumour burden and metastasis formation by bioluminescence, and the in vivo characteristics of these cell lines has been described in detail[11]. This model is amenable to several types of genomic analysis, and here it has been used for the identification of differences in gene expression between mammary gland primary tumours derived from the metastatic 4T1 and 66cl4 cell lines versus the non-metastatic 67NR cell line.

FIG. 1, part a, depicts a table of relative expression values for gene following analysis of primary breast cancer tumour tissue from three individual mice from each of three cell models (4T1, 66cl4, 67NR). Tissue was analyzed using a mouse-specific gene microarray platform. To minimize the confounding effects of the heterogeneity of the stromal and normal tissue components, total RNA was isolated from laser capture microdissected tumour tissue, as described previously[11], from tumours of equal size. Differential gene expression patterns were analyzed according to parameters published previously[11]. Differential expression of hypoxia-induced genes is shown, with relative gene expression indicated using a scale from 1 (low expression) to 10 (high expression).

FIG. 1, part b, depicts corresponding microarray data for FIG. 1, part a. DNA microarray analysis using the Affymetrix platform resulted in the identification of several genes that are differentially expressed between the metastatic and non-metastatic tumours. The data have been submitted to the Gene Expression Omnibus database (GSE 11259). Among the differentially expressed genes, a significant number of hypoxia inducible genes were identified. Carbonic anhydrase 9 (CAIX) and carbonic anhydrase 12 (CAXII) are prominent markers of hypoxia[12,13,23]. Other interesting genes in this group are VEGF-C, Ephrin A5, EphB2, tenascin C, TGF-β3, pyruvate dehydrogenase kinase 3, keratin 14 and hypoxia inducible factor 1 alpha subunit[12,14,15,16,17].

The differential expression of genes observed in the microarray analysis was validated by qRT-PCR (n=3) for each tumour type.

FIG. 2, part a, depicts confirmation of the differential expression of some of these genes by qRT-PCR. Total RNA was extracted from primary tumor tissue from the 3 models and the differential expression of hypoxia inducible genes observed in the microarray analysis was validated by qRT-PCR; n=3 for each tumor type; error bars indicate standard error of the mean (s.e.m.).

FIG. 2, part b, depicts protein expression analysis of CAIX in whole tissue extracts from the primary tumours used for gene expression analysis, as evaluated by Western blot, with β-actin used as a loading control (NMG=normal mammary gland control).

FIG. 2, part c, shows confirmation of protein expression by immunohistochemistry for CAIX performed on sections of primary tumour tissue from the three models. Representative images demonstrate prominent staining of the cell membrane (arrowheads) in tumours formed by the metastatic cell lines (scale bar=50 μm).

FIG. 2, part d, depicts expression of HIF-1α in whole tissue extracts from the primary tumours used for gene expression analysis. Hypoxia induces gene expression primarily through the stabilization of the hypoxia inducible factors 1 and 2 (HIF-1 and 2) transcription factors. Therefore, the expression of HIF1 and 2 was examined in the primary tumours. Expression of HIF-1α in whole tissue extracts from the primary tumours used for gene expression analysis was evaluated by Western blot using β-actin as a loading control. Vertical lines mark the juxtaposition of non-contiguous lanes. The expression of HIF-1α is elevated in the metastatic 4T1 tumours relative to the 67NR non-metastatic tumours. The expression of both HIF-1α and CAIX are higher in the 4T1 tumours compared to the non-metastatic 67NR tumours (see also FIG. 2, part b).

Example 2

Primary Tumour Characterization

The differential expression of hypoxia inducible genes in the metastatic tumours versus the non-metastatic tumours, led us to investigate the extent of hypoxia, necrosis, apoptosis, proliferation, vascularization and lymphangiogenesis in 4T1, 66cl4 and 67NR tumours. Tumours were grown and labeled in vivo for proliferation (BrdU), hypoxia (pimonidazole) and perfusion (DiOC$_7$). Immunohistochemistry for CD31 (vasculature) and in situ detection of TUNEL (apoptosis) were then performed. Necrosis was assessed by histology. Representative composite, pseudocolored images demonstrated the presence of each marker. Ten individual 67NR, 66cl4 or 4T1 tumours were sectioned and stained for the above parameters.

FIG. 3, part a, depicts whole tumour averages for microvessel density (MVD) as determined by CD31 staining, proliferation as determined by BrdUrd staining, hypoxia as determined by pimonidazole staining, apoptosis as determined by TUNEL labeling, and % necrosis as determined by histology. Data are expressed as the averages of whole tumour sections excluding necrotic areas±s.e.m. n=10 for each tumour type. The non-metastatic 67NR primary tumours exhibit high vascular density, are largely devoid of hypoxia, and have low numbers of apoptotic cells. In sharp contrast, primary tumours derived from 66cl4 and especially 4T1 metastatic cell lines, were overall poorly vascularized, and had large areas of hypoxia and necrosis with high numbers of apoptotic cells. There was no difference in the overall proliferation index between the three tumour types.

Because of the elevated levels of VEGF-C in the metastatic tumours (see FIG. 7), the extent of lymphangiogenesis was investigated in the tumours with an anti-LYVE antibody which detects an antigen expressed on the surfaces of lymphatic endothelial cells.

FIG. 3, part b, depicts immunohistochemistry for LYVE-1 and CD31 as performed on sections of primary tumours from the 4T1 and 67NR tumour models (scale bar=1 mm). Tissue sections were counterstained with DAPI. Representative images demonstrate the presence of intratumoral lymphatic vessels (arrowheads) in the 4T1 tumours. Well developed intratumoral lymphatic vessels were only detected in the primary tumours derived from the highly metastatic 4T1 cells, which express the highest levels of VEGF-C (see FIG. 7). The anti-LYVE antibody detects a number of single cells in both the 66cl4 and 67NR tumours, which is attributable to the presence of macrophages, which are more prominent in the 66cl4 and 67NR tumours relative to the 4T1 tumours.

Data presented herein implicate hypoxia as a metastatic stimulus. Contrary to accepted paradigms, high vascular density may provide a favorable environment for tumour growth in situ, precluding the need to metastasize, whereas a severe hypoxic or necrotic microenvironment results in greater metastatic potential by encouraging escape from a toxic environment. The ability to survive in a hypoxic microenvironment appears to drive tumour cells to more favorable environments. The formation of intratumoral lymphatics may provide additional mechanisms for metastasis. In this regard, lymphangiogenesis is also a poor prognostic marker for breast cancer, and is known to facilitate metastasis[14]. The hypoxia-induced expression of CAIX and XII could be essential factors in the survival of the tumour cells under these conditions.

Example 3

Carbonic Anhydrase IX as a Driver of Metastatic Potential

The differential expression of CAIX in the metastatic versus the non-metastatic primary tumours, led to investigation of whether the differences in hypoxia induced CAIX expression in the metastatic and non-metastatic tumours are innate properties of the cells or whether they are acquired in vivo. The three cell lines were cultured under normoxic or hypoxic conditions for various time periods and the expression of CAIX, as well as other hypoxia inducible proteins, was determined.

FIG. 4, part a, shows levels of gene expression as determined by quantitative RT-PCR (qRT-PCR); n=3. Error bars indicate s.e.m. The indicated cell lines were cultured in normoxia or hypoxia for 48 hours. Data shown are representative of three independent experiments. CAIX expression was readily induced after 48 hours in hypoxia in both 66cl4 and 4T1 metastatic cells, but was not induced in the non-metastatic 67NR cells. Similarly, the expression of CAXII and tenascin-C were also differentially regulated by hypoxia in the metastatic versus the non-metastatic cells. These data suggest that the cell lines may regulate the expression of hypoxia inducible factors (HIFs) differentially.

FIG. 4, part b, shows stabilization of HIF-1α protein as determined by Western blot. In the indicated cell lines cultured in hypoxia for 0-4 hours (h). Alternatively, cells were cultured in normoxia (N) or hypoxia (H) for 72 hours and induction of CAIX was assayed by Western blot. β-actin was used as a loading control. Hypoxia induced the expression of HIF-1α more rapidly and to a higher level in the 66cl4 and the 4T1 cells, compared to the 67NR cells, suggesting that differential regulation of HIF-1α stabilization may be responsible for differential expression of the hypoxia inducible genes, such as CAIX.

Carbonic anhydrases catalyze the reversible hydration of cellular carbon dioxide into protons and bicarbonate ions. CAIX and XII are membrane associated, and CAIX is functionally linked to regulation of the extracellular pH[18]. Hypoxia-induced, extracellular acidification has been implicated in more aggressive behavior of tumour cells in terms of extracellular matrix remodeling and invasion[19]. Experiments were therefore conducted to determine whether hypoxia would induce acidification of the extracellular medium in the three different cell lines.

FIG. 4, part c, shows the pH of culture medium of cells which were cultured in normoxia or hypoxia for 72 hours in the absence or presence of the inhibitor, CAI 17, at concentrations of 400, 600 and 400 μM for the 4T1, 66cl4 and 67NR cells, respectively. Data are expressed as the mean change in extracellular pH±s.e.m. of triplicate samples and are representative of 3 independent experiments. Asterisks indicate $P<0.001$ with a two-sided Student's t-test, compared to cells cultured without inhibitor. The extracellular pH decreased dramatically under hypoxia in the 66cl4 and the 4T1 metastatic cell lines, but remained unchanged in the 67NR cultures.

FIG. 4, part d, depicts localization of the fluorescent CAIX inhibitor, CAI 17, on cells. To determine whether the acidification was CAIX-dependent, cells were treated with a highly specific CAIX inhibitor (compound 17 or "CAI 17")[20]. Cells were incubated in normoxia or hypoxia for 72 hours in the presence of CAI 17 at a concentration of 10 μM. Shown are representative images of the FITC-tagged inhibitor bound to the cells under the indicated experimental conditions. Data were similar in 3 independent experiments. CAI 17 is a fluorescent inhibitor which binds to active CAIX and binds to the cell surfaces of 66cl4 and 4T1 cells under hypoxia, but not the 67NR non-metastatic cells.

FIG. 4, part e, shows change in culture medium pH for 4T1 cells transfected with non-silencing shRNA (NS) and 4T1 clones (clones 1, 2, 4 and 5) transfected with CAIX shRNA cultured in normoxia or hypoxia for 72 hours. Data are expressed as the mean change in extracellular pH±s.e.m. and are representative of 2 independent experiments (each n=3). Treatment of the cells with this inhibitor reversed acidification of the extracellular medium under hypoxia in the 66cl4 and 4T1 cell cultures (see FIG. 3C).

Silencing of CAIX gene expression was carried out by stable expression of CAIX shRNA in the 4T1 cells. Several independent clones of 4T1 cells that express the shRNA were derived.

FIG. 5, part a, shows GFP production in 4T1 cells transfected with shRNA targeting mouse CAIX or a non-silencing control sequence as a means of demonstrating successful transfection. Representative images of cells are shown. Parallel phase contrast images are shown to demonstrate that all cells express GFP, a surrogate marker for expression of the shRNA.

FIG. 5, part b, shows CAIX mRNA expression in 4T1 cells expressing non-silencing shRNA (NS) or shRNA targeting CAIX (clone 2 and clone 5) following incubated for 72 hours in normoxia or hypoxia. Total RNA was extracted and the expression of CAIX was measured by qRT-PCR. n=3; error bars indicate s.e.m.

FIG. 5, part c, shows Western blot analysis of CAIX expression in 4T1 cells expressing non-silencing shRNA (NS) or shRNA targeting CAIX ("shCAIX") incubated for 72 hours in normoxia (N) or hypoxia (H). Total cell lysates were assessed by Western blot for CAIX expression and β-actin was used as a loading control.

FIG. 5, part d, shows tumour growth for parental 4T1 cells, 4T1 cells expressing non-silencing shRNA, and two different clones expressing CAIX shRNA (clone 2 and clone 5) were monitored for tumour growth. Plots show tumour volume in $mm^3$ derived from caliper measurements as a function of time post-implantation. "n" for each group at the time of tumour cell inoculation is indicated. Arrows denote changes in the number of mice at the indicated time points for the two groups expressing CAIX shRNA. The revised value is listed at the top of each arrow. Results are expressed as means±s.e.m. for each cohort. Single asterisks denotes the time of all tumours removed from parental 4T1 and non-silencing shRNA groups. *** indicates $p<10^{-11}$ with a two-sided Student's t-test, compared to the non-silencing shRNA tumours. CAIX expression in these clones expressing CAIX-targeting shRNA is depleted relative to parental cells and cells expressing a non-silencing control RNA, with significant suppression of CAIX expression under hypoxic conditions. There was no significant difference in the basal growth properties of the shCAIX expressing cells compared to the wild-type or the non-silencing control cells.

FIG. 6, part a, shows over-expression of CAIX in 67NR cells. Immunocytochemistry for human CAIX (hCAIX) performed on parental 67NR cells and 67NR cells expressing hCAIX. Representative images are shown and demonstrate robust hCAIX expression in transfected cells (right panel). Nuclei are counterstained with DAPI and are clearly visible in the left panel (scale bar=50 μm). CAIX is clearly expressed under both normoxic and hypoxic conditions in these variants as compared to the parental 67NR cells.

FIG. 6, part b, shows that CAIX over-expressing 67NR cells have constitutive acidification of the extracellular medium relative to the parental cells. Culture change in culture medium pH for 67NR hCAIX-expressing cells was measured following culturing in normoxia or hypoxia for 72 hours with or without 600 μm CAI 17, n=3. Data are expressed as the mean change in extracellular pH±s.e.m. In contrast, acidification of the extracellular medium under hypoxia is completely blocked in the CAIX shRNA expressing 4T1 clones relative to the parental and non-silencing RNA expressing 4T1 cells (see FIG. 4, part e), and more closely resembles the response of the non-metastatic parental 67NR cells (see FIG. 4, part c). These results demonstrate that the metastatic cell lines can respond to hypoxia by inducing CAIX expression and CAIX-dependent acidification of the extracellular medium, whereas non-metastatic cells are unable to induce this response.

It has been determined that hypoxic tumours generate microenvironments that promote metastasis, and CAIX has been identified as an essential regulator of tumour cell survival in this microenvironment. Results demonstrate that CAIX is a targetable biomarker for breast cancer metastatic potential, allowing for the identification and selection of patients whose tumours are likely to metastasize, for treatment with CAIX inhibitors to prevent this deadly process. As such, the development of small molecule inhibitors of CAIX activity[20], anti-CAIX neutralizing antibodies, and CAIX imaging agents, which may have clinical utility is fully contemplated herein. Likewise, small molecular inhibitors, neutralizing antibodies, imaging agents, etc. of other biomarkers disclosed herein, particularly those up-regulated in aggressive tumours, may also (alone or in combination) have clinical utility and are fully contemplated herein.

Example 4

Silencing CAIX Expression Regresses Primary Tumour Growth and Inhibits Metastases Formation.

FIG. 5, part d, shows the growth and metastatic properties of the CAIX depleted and control 4T1 cells in vivo was tested. The parental 4T1 and control 4T1 cells expressing non-silencing shRNA readily formed primary tumours in the mammary glands of BalbC mice, and grew steadily over 30 days. In sharp contrast, the clones in which CAIX expression was depleted (see FIG. 5, part a) with stable expression of CAIX specific shRNA stopped growing and regressed significantly after initial tumour growth (see FIG. 5, part b). The onset of the regression of the tumour growth coincided with the onset of hypoxia in the tumours at approximately 15 days post inoculation of the cells in the mammary gland.

FIG. 7, part a, depicts primary and metastatic tumour formation in an orthotopic breast cancer model. Representative in vivo bioluminescent images of primary and metastatic tumours derived from control breast cancer cells (Parental, NS shRNA) and cells expressing shCAIX (clone 2 and clone 5) are shown. The primary tumours were removed 3 to 4 weeks post-inoculation. Signals are displayed as pseudo-color heat map images (blue, least intense; red, most intense; $\times 10^6$ photons/second) overlaid on gray-scale body images. After removal of the primary breast tumours, metastases in several organs were readily visible in mice that had been inoculated with the parental 4T1 or the non-silencing control expressing 4T1 cells. However, no metastases were observed for up to 100 days in mice that had been inoculated with the CAIX depleted clones. In addition regression of the tumours appeared to be permanent, as there was no recurrence of primary tumours 80 days post inoculation (see FIG. 5, part d and Table 1).

TABLE 1

Summary of tumour occurrence and metastasis in control and CAIX depleted mammary tumours up to 80 days post tumour inoculation

| Tumour type | PT occurrence | PT complete regression | PT removed | PT recurrence | Tumour metastasis |
|---|---|---|---|---|---|
| 4T1 | 9/9 | 0/9 | 9/9 | 5/9 | 5/9 |
| 4T1-nonSilencing shRNA | 10/10 | 0/10 | 10/10 | 5/9 | 5/9 |

TABLE 1-continued

Summary of tumour occurrence and metastasis in control and CAIX depleted mammary tumours up to 80 days post tumour inoculation

| Tumour type | PT occurrence | PT complete regression | PT removed | PT recurrence | Tumour metastasis |
|---|---|---|---|---|---|
| 4T1-CAIXshRNA-clone 2 | 10/10 | 5/10 | 5/10 | 0/8 | 0/8 |
| 4T1-CAIXshRNA-clone 5 | 10/10 | 8/10 | 2/10 | 0/10 | 0/10 |

FIG. 7, part b, shows that elimination of CAIX expression had a dramatic effect on the overall survival of the mice. Control animals and animals inoculated with shCAIX-expressing cells were monitored for survival. The plot shows the percentage of mice surviving in each of the two study arms (pooled control and pooled shCAIX groups) as a function of time. Each "step" represents humane sacrifice of a sick animal due to metastatic spread of disease. n=18 for each group.

FIG. 7, part c, shows expression of CAIX in whole tissue extracts from the primary tumors formed by parental and 4T1 cells expressing non-silencing shRNA (NS) or shRNA targeting CAIX. Expression was evaluated by Western blot, with β-actin used as a loading control. Examination of the primary tumours from the control and the CAIX depleted cells, confirmed down-regulation of CAIX expression in the shCAIX 4T1 tumours. Furthermore, tumour cell apoptosis in non-necrotic regions of the CAIX depleted tumours was accelerated relative to the control tumours.

FIG. 7, part d, shows that, indeed, 4T1 cells depleted of CAIX showed increased apoptosis compared to non-silencing control cells when cultured in hypoxia. 4T1 cells expressing non-silencing shRNA (NS) or shRNA targeting CAIX were plated onto coverslips and incubated for 48 hours in normoxia (N) or hypoxia (H) in the presence of reduced serum. Representative images with TUNEL-positive cells (indicated with arrows) are shown in the left panel ("TUNEL").

FIG. 7, part e, shows the number of apoptotic cells as quantified by counting 5 random fields per cell line at 20× magnification. Quantitative data is shown as fold increase in TUNEL-positive cells in cells expressing CAIX shRNA when compared to non-silencing control cells. n=5. * indicates P<0.01 with a two-sided Student's t-test, compared to the non-silencing control sample. Data is representative of 2 independent experiments. Interestingly, constitutive overexpression of human CAIX in the non-metastatic 67NR cells did not have any effect on tumour growth or metastasis. These data suggest that the requirement of CAIX for tumour growth and metastasis relates to the hypoxic microenvironment per se, and that CAIX is not required for survival of cells in non-hypoxic tumours.

Thus, an essential role of carbonic anhydrase IX in the survival of the tumour cells in hypoxic microenvironments has been identified. For the first time, it has been shown that silencing CAIX expression results in breast tumour regression and subsequent loss of metastasis formation. Preventing CAIX expression severely curtails the ability to metastasize and induces tumour cell death. This hypoxia-specific requirement of CAIX is strengthened by our findings that overexpression of CAIX per se in a non-hypoxic tumour (for example, in 67NR cells), has no effect on tumour growth and metastasis. Results demonstrate that CAIX is a targetable biomarker for breast cancer metastatic potential.

Example 5

CAIX Expression is an Independent Prognostic Marker for Distant Metastasis and Overall Survival in Breast Cancer The expression of CAIX by immunohistochemistry (IHC) was investigated in 3,992 primary breast tumour tissue microarray (TMA) with a median follow-up of 10.5 years.

Table 2 sets out baseline demographics, standard pathological prognostic factors and adjuvant treatments prescribed for this patient cohort.

TABLE 2

Baseline demographics for breast cancer patient cohort

| | | CA-IX (scored at the B.C. Cancer Agency, Vancouver, Canada, July 2005) | |
|---|---|---|---|
| | n = 3630 | negative | any positive |
| age at diagnosis (groupings) | <40 | 192 (70.8%) | 79 (29.2%) |
| | 40-49 | 650 (83%) | 133 (17%) |
| | 50-65 | 1096 (84.7%) | 198 (15.3%) |
| | >65 | 1126 (87.8%) | 156 (12.2%) |
| menstrual status | unknown (documented) | 74 (90.2%) | 8 (9.76%) |
| | premenopausal | 869 (79.7%) | 222 (20.3%) |
| | postmenopausal | 2120 (86.3%) | 336 (13.7%) |
| | pregnant | 1 (100%) | 0 (0%) |
| tumour size (groupings) | unknown | 19 (82.6%) | 4 (17.4%) |
| | <=2 cm | 1646 (87.6%) | 232 (12.4%) |
| | >2-5 cm | 1244 (81%) | 291 (19.0%) |
| | >5 cm | 155 (79.9%) | 39 (20.1%) |
| nodal status | nodal status unknown | 5 (62.5%) | 3 (37.5%) |
| | node negative | 1722 (84.6%) | 314 (15.4%) |
| | node positive | 1337 (84.3%) | 249 (15.7%) |
| grade | unknown | 144 (94.1%) | 9 (5.88%) |
| | grade 1 | 163 (95.3%) | 8 (4.68%) |
| | grade 2 | 1247 (89%) | 153 (10.9%) |
| | grade 3 | 1510 (79.2%) | 396 (20.8%) |
| type of surgery | no initial breast surgery | 47 (81%) | 11 (19.0%) |
| | complete mx | 1653 (85%) | 292 (15%) |
| | partial mx | 1364 (83.8%) | 263 (16.2%) |
| adjuvant systemic therapy | no systemic therapy | 1267 (83.8%) | 245 (16.2%) |
| | Tam; no chemo | 1029 (89.5%) | 121 (10.5%) |
| | Chemo; no horm | 524 (76.4%) | 162 (23.6%) |
| | Chemo + Tam | 229 (85.8%) | 38 (14.2%) |
| | other | 15 (100%) | 0 (0%) |
| adjuvant radiation | no initial breast/chest wall or nodal RT | 1292 (85.7%) | 215 (14.3%) |
| | any initial breast/chest wall or nodal RT | 1772 (83.5%) | 351 (16.5%) |

Table 3 shows that CAIX expression was seen in 15.6% of assessable tumours. CAIX was differentially expressed among the biological subtypes, with the highest correlation in the basal breast cancers (51%) and the lowest proportion in the luminal A subtype (8%).

TABLE 3

CAIX expression according to biological subtype

| Breast Cancer Subtype | Total N | N CAIX +ve | % CAIX +ve |
|---|---|---|---|
| LumA (ER or PR+, Her2−, ki67−) | 1437 | 120 | 8 |
| LumB (ER or PR+, Her2−, ki67+) | 815 | 88 | 11 |
| Lum/HER2+ (Her2+, ER or PR+) | 213 | 36 | 17 |
| Her2+ (Her2+, ER−, PR−) | 239 | 80 | 33 |
| Basal (ER−, PR−, Her2−, CK56 or EGFR+) | 327 | 168 | 51 |

FIG. 8, part a, shows a Kaplan-Meier plot depicting cumulative survival (Cum Survival) as a function of relapse-free survival (RFS) time to event. The cut off for data was at 10 years post-diagnosis. The CAIX positive group (light line) was significantly associated with a worse relapse-free survival compared to the CAIX negative group (dark line) ($p<10^{-17}$).

FIG. 8, part b, shows a Kaplan-Meier plot depicting cumulative survival (Cum Survival) as a function of relapse-free survival time to a distant metastatic event ("distant RFS"). The cut off for data was at 10 years post-diagnosis. The CAIX positive group (light line) was significantly associated with a worse survival time to a distant metastatic event compared to the CAIX negative group (dark line) ($p<10^{-16}$).

FIG. 8, part c, shows a Kaplan-Meier plot depicting cumulative survival (Cum Survival) as a function of overall survival time (distant site survival or "DSS" time to event). The cut off for data at 10 years post-diagnosis. CAIX expression was also associated with worse overall survival ($p<10^{-13}$).

For the purposes of analysis, CAIX expression on the TMA was binarized as 0 and 1-3. The 10 year distant relapse free survival and overall survival rates in the CAIX positive versus CAIX negative groups were 57% compared to 73%, and 52% compared to 65%, respectively.

Table 4 shows that, in multivariate analyses including all standard prognostic variables and biological subtypes, CAIX expression was still a strong independent poor prognostic factor with a hazard ratio of 1.4.

FIG. 9 shows representative examples of human breast cancer tissue cores from the TMA stained for CAIX. Positive staining is denoted by the intense dark regions.

Thus, interrogation of CAIX expression in the primary tumours of one of the largest cohorts of breast cancer patient tumour samples demonstrates that CAIX is an independent poor prognostic factor for relapse-free survival time, survival time to distant metastasis, and overall breast cancer survival. In addition, these data demonstrate a clear link of CAIX expression to a higher rate of distant metastasis. CAIX expression falls clearly into the basal-like breast tumour group[23], but in a subgroup that is distinct from those expressing Her2[23]. Since CAIX expression is considered as a surrogate marker for hypoxia[23,32,33], it should be possible to identify and select patients whose primary breast tumours are hypoxic and, based on findings presented herein, more likely to metastasize.

REFERENCES

1. Chambers, A. F., Groom, A. C. & MacDonald, I. C. Dissemination and growth of cancer cells in metastatic sites. *Nat Rev Cancer* 2 8, 563-572 (2002).
2. Ramaswamy, S., Ross, K. N., Lander, E. S. & Golub, T. R. A molecular signature of metastasis in primary solid tumors. *Nat Genet.* 33 1, 49-54 (2003).
3. van 't Veer, L. J., et al. Gene expression profiling predicts clinical outcome of breast cancer. *Nature* 415 6871, 530-536 (2002).
4. van de Vijver, M. J., et al. A gene-expression signature as a predictor of survival in breast cancer. *N Engl J Med* 347 25, 1999-2009 (2002).
5. Wang, Y., et al. Gene-expression profiles to predict distant metastasis of lymph-node-negative primary breast cancer. *Lancet* 365 9460, 671-679 (2005).
6. Nguyen, D. X., Bos, P. D. & Massague, J. Metastasis: from dissemination to organ-specific colonization. *Nat Rev Cancer* 9 4, 274-284 (2009).
7. Gupta, G. P., et al. Mediators of vascular remodelling co-opted for sequential steps in lung metastasis. *Nature* 446 7137, 765-770 (2007).

TABLE 4

CA9 10-year distant DFS (disease free survival) & breast cancer specific survival (Cox model)

| | 10 years distant relapse free survival | | 10 years breast cancer specific survival | |
|---|---|---|---|---|
| | hazard ratio (95% C.I.) | p-value | hazard ratio (95% C.I.) | p-value |
| age (years) | 1.003 (0.997-1.008) | 0.311 | 1.006 (1.000-1.012) | 0.051 |
| grade {1 or 2} vs. {3} | 1.464 (1.254-1.709) | 1.4E−6 | 1.633 (1.371-1.944) | 3.83E−8 |
| LVI status | 1.236 (1.055-1.450) | 8.96E−3 | 1.239 (1.040-1.475) | 0.016 |
| nodal status | 2.114 (1.801-2.482) | 5.56E−20 | 2.275 (1.905-2.715) | 9.8E−20 |
| tumour size | | | | |
| {≤2 cm} vs. {>2 to 5 cm} | 1.584 (1.366-1.838) | 1.21E−9 | 1.636 (1.389-1.928) | 3.88E−9 |
| {≤2 cm} vs. {>5 cm} | 1.816 (1.366-2.414) | 3.95E−5 | 1.890 (1.398-2.554) | 3.44E−5 |
| breast cancer subtype (IHC panel) | | | | |
| Luminal A vs. Luminal B/Ki67 | 1.705 (1.433-2.028) | 1.77E−9 | 1.866 (1.533-2.273) | 5.26E−10 |
| Luminal A vs. Luminal B/Her2 | 1.810 (1.402-2.335) | 5.1E−6 | 2.066 (1.566-2.728) | 2.98E−7 |
| Luminal A vs. Her2+/ER− | 2.343 (1.851-2.967) | 1.56E−12 | 2.795 (2.163-3.612) | 3.98E−15 |
| Luminal A vs. Basal | 1.679 (1.309-2.154) | 4.55E−5 | 2.375 (1.823-3.096) | 1.54E−10 |
| CAIX {0} vs. {1, 2, 3} | 1.457 (1.225-1.733) | 2.09E−5 | 1.425 (1.182-1.718) | 2.06E−4 |

8. Minn, A. J., et al. Genes that mediate breast cancer metastasis to lung. *Nature* 436 7050, 518-524 (2005).
9. Eckhardt, B. L., et al. Genomic analysis of a spontaneous model of breast cancer metastasis to bone reveals a role for the extracellular matrix. *Mol Cancer Res* 3 1, 1-13 (2005).
10. Aslakson, C. J. & Miller, F. R. Selective events in the metastatic process defined by analysis of the sequential dissemination of subpopulations of a mouse mammary tumor. *Cancer Res* 52 6, 1399-1405 (1992).
11. Lou, Y., et al. Epithelial-mesenchymal transition (EMT) is not sufficient for spontaneous murine breast cancer metastasis. *Dev Dyn* 237 10, 2755-2768 (2008).
12. Kroemer, G. & Pouyssegur, J. Tumor cell metabolism: cancer's Achilles' heel. Cancer *Cell* 13 6, 472-482 (2008).
13. Chiche, J., et al. Hypoxia-inducible carbonic anhydrase 1× and XII promote tumor cell growth by counteracting acidosis through the regulation of the intracellular pH. *Cancer Res* 69 1, 358-368 (2009).
14. Achen, M. G., McColl, B. K. & Stacker, S. A. Focus on lymphangiogenesis in tumor metastasis. *Cancer Cell* 7 2, 121-127 (2005).
15. Alitalo, K., Tammela, T. & Petrova, T. V. Lymphangiogenesis in development and human disease. *Nature* 438 7070, 946-953 (2005).
16. Tavazoie, S. F., et al. Endogenous human microRNAs that suppress breast cancer metastasis. *Nature* 4517175, 147-152 (2008).
17. Ghellal, A., et al. Prognostic significance of TGF beta 1 and TGF beta 3 in human breast carcinoma. *Anticancer Res* 20 6B, 4413-4418 (2000).
18. Pastorekova, S., Ratcliffe, P. J. & Pastorek, J. Molecular mechanisms of carbonic anhydrase IX-mediated pH regulation under hypoxia. *BJU Int* 101 Suppl 4, 8-15 (2008).
19. Gatenby, R. A. & Gillies, R. J. A microenvironmental model of carcinogenesis. *Nat Rev Cancer* 8 1, 56-61 (2008).
20. Supuran, C. T. Carbonic anhydrases: novel therapeutic applications for inhibitors and activators. *Nat Rev Drug Discov* 7 2, 168-181 (2008).
21. Choi, S. W., et al. Expression of carbonic anhydrase IX is associated with postoperative recurrence and poor prognosis in surgically treated oral squamous cell carcinoma. *Hum Pathol* 39 9, 1317-1322 (2008).
22. Kon-no, H., et al. Carbonic anhydrase IX expression is associated with tumor progression and a poor prognosis of lung adenocarcinoma. *Lung Cancer* 54 3, 409-418 (2006).
23. Tan, E. Y., et al. The key hypoxia regulated gene CAIX is upregulated in basal-like breast tumours and is associated with resistance to chemotherapy. *Br J Cancer* 100 2, 405-411 (2009).
24. Chia, S. K., et al. Prognostic significance of a novel hypoxia-regulated marker, carbonic anhydrase IX, in invasive breast carcinoma. *J Clin Oncol* 19 16, 3660-3668 (2001).
25. Mazzone, M., et al. Heterozygous deficiency of PHD2 restores tumor oxygenation and inhibits metastasis via endothelial normalization. *Cell* 136 5, 839-851 (2009).
26. Galluzzo, M., Pennacchietti, S., Rosano, S., Comoglio, P. M. & Michieli, P. Prevention of hypoxia by myoglobin expression in human tumor cells promotes differentiation and inhibits metastasis. *J Clin Invest* 119 4, 865-875 (2009).
27. Ebos, J. M., et al. Accelerated metastasis after short-term treatment with a potent inhibitor of tumor angiogenesis. *Cancer Cell* 15 3, 232-239 (2009).
28. Paez-Ribes, M., et al. Antiangiogenic therapy elicits malignant progression of tumors to increased local invasion and distant metastasis. *Cancer Cell* 15 3, 220-231 (2009).
29. Reynolds, A. R., et al. Stimulation of tumor growth and angiogenesis by low concentrations of RGD-mimetic integrin inhibitors. *Nat Med* 15 4, 392-400 (2009).
30. Loges, S., Mazzone, M., Hohensinner, P. & Carmeliet, P. Silencing or fueling metastasis with VEGF inhibitors: antiangiogenesis revisited. *Cancer Cell* 15 3, 167-170 (2009).
31. Potter, C. P. & Harris, A. L. Diagnostic, prognostic and therapeutic implications of carbonic anhydrases in cancer. *Br J Cancer* 89 1, 2-7 (2003).
32. Lal, A., et al. Transcriptional response to hypoxia in human tumors. *J Natl Cancer Inst* 93 17, 1337-1343 (2001).
33. Wykoff, C. C., et al. Hypoxia-inducible expression of tumor-associated carbonic anhydrases. *Cancer Res* 60 24, 7075-7083 (2000).
34. Svastova, E., et al. Hypoxia activates the capacity of tumor-associated carbonic anhydrase IX to acidify extracellular pH. *FEBS Lett* 577 3, 439-445 (2004).
35. McPhee, T. R., McDonald, P. C., Oloumi, A. & Dedhar, S. Integrin-linked kinase regulates E-cadherin expression through PARP-1. *Dev Dyn* 237 10, 2737-2747 (2008).

All documents referred to herein are incorporated by reference.

In the preceding description, for purposes of explanation, numerous details are set forth in order to provide a thorough understanding of the embodiments. However, it will be apparent to one skilled in the art that these specific details are not required. The above-described embodiments are intended to be examples only. Alterations, modifications and variations can be effected to the particular embodiments by those of skill in the art without departing from the scope, which is defined by the claims appended hereto.

What is claimed is:

1. A method of treating a subject for cancer, based on measured expression levels of indicators of metastatic potential in a tumour tissue sample from said subject, said method comprising:
    (a) administering a non-aggressive treatment to said subject, if expression levels of indicators of moderate metastatic potential and indicators of high metastatic potential are less than or substantially equal to a control,
    (b) administering a moderately aggressive treatment to the subject, if expression levels of said indicators of moderate metastatic potential are elevated compared to said control, and said expression levels of said indicators of high metastatic potential are less than or equal to said control, or
    (c) administering a highly aggressive treatment to the subject, if expression levels of said indicators of moderate metastatic potential and said indicators of high metastatic potential are elevated compared to said control;
wherein
    (i) the indicators of moderate metastatic potential are CAIX and VEGF-C, and optionally one or more indicators selected from the group consisting of EFNA5, EPHB2, TGF-β3, and PDK3, and
    (ii) the indicators of high metastatic potential are CAXII, KRT14, and TNC, and optionally HIF-1α.

2. The method of claim 1, wherein said measured expression levels comprise measured protein or mRNA expression levels.

3. The method of claim 1, wherein said tumour tissue sample is from a human breast cancer tumour.

4. The method of claim 1, wherein expression levels of CAIX, CAXII, VEGF-C, EFNA5, EPHB2, TNC, TGF-β3, PDK3, KRT14, and HIF-1α are measured.

5. The method of claim 1, wherein said highly aggressive treatment or said moderately aggressive treatment comprises administering an inhibitor of at least one indicator of moderate metastatic potential or of at least one indicator of high metastatic potential.

6. The method of claim 5, wherein said highly aggressive treatment or said moderately aggressive treatment comprises an inhibitor of CAIX or CAXII.

7. A method of treating a subject for cancer comprising:
I. measuring expression levels in a tumour tissue sample of indicators of metastatic potential, wherein said step of measuring comprises measuring expression levels of
　(i) indicators of moderate metastatic potential which are CAIX and VEGF-C, and optionally one or more indicators selected from the group consisting of EFNA5, EPHB2, TGF-β3, and PDK3, and
　(ii) indicators of high metastatic potential which are CAXII, KRT14, and TNC, and optionally HIF-1α;
II. comparing said expression levels to a control to determine metastatic potential, and determining:
　(a) low metastatic potential if expression levels of said indicators of moderate metastatic potential and said indicators of high metastatic potential of both types of indicators are less than or substantially equal to said control,
　(b) moderate metastatic potential if said expression levels of said indicators of moderate metastatic potential are elevated compared to said control, and said expression levels of said indicators of high metastatic potential are less than or equal to said control, or
　(c) high metastatic potential if said expression levels of said indicators of moderate metastatic potential and said indicators of high metastatic potential are elevated compared to said control:
III. administering a treatment, comprising:
　(a) administering a non-aggressive cancer treatment if expression levels of said indicators of moderate metastatic potential and said indicators of high metastatic potential are less than or substantially equal to said control,
　(b) administering a moderately aggressive cancer treatment regime if said expression levels of said indicators of moderate metastatic potential are elevated compared to said control, and said expression levels of said indicators of high metastatic potential are less than or equal to said control, or
　(c) administering a highly aggressive cancer treatment regime if said expression levels of indicators of moderate metastatic potential and said indicators of high metastatic potential are elevated compared to said control.

8. A method of treating a subject for cancer comprising:
I. requesting a test that measures expression levels of indicators of metastatic potential in a tumour tissue sample, and that compares said expression levels to a control to determine metastatic potential,
　wherein said test measures expression levels of
　　(i) indicators of moderate metastatic potential which are CAIX and VEGF-C, and optionally one or more indicators selected from the group consisting of EFNA5, EPHB2, TGF-β3, and PDK3, and
　　(ii) indicators of high metastatic potential which are CAXII, KRT14, and TNC, and optionally HIF-1α;
　wherein the results indicate:
　　(a) low metastatic potential if expression levels of said indicators of moderate metastatic potential and said indicators of high metastatic potential of both types of indicators are less than or substantially equal to said control,
　　(b) moderate metastatic potential if said expression levels of said indicators of moderate metastatic potential are elevated compared to said control, and said expression levels of said indicators of high metastatic potential are less than or equal to said control, or
　　(c) high metastatic potential if said expression levels of said indicators of moderate metastatic potential and said indicators of high metastatic potential are elevated compared to said control;
II. administering a treatment, comprising:
　(a) administering a non-aggressive cancer treatment if expression levels of said indicators of moderate metastatic potential and said indicators of high metastatic potential are less than or substantially equal to said control,
　(b) administering a moderately aggressive cancer treatment regime if said expression levels of said indicators of moderate metastatic potential are elevated compared to said control, and said expression levels of said indicators of high metastatic potential are less than or equal to said control, or
　(c) administering a highly aggressive cancer treatment regime if said expression levels of indicators of moderate metastatic potential and said indicators of high metastatic potential are elevated compared to said control.

* * * * *